US012245883B2

(12) United States Patent
Moshe et al.

(10) Patent No.: US 12,245,883 B2
(45) Date of Patent: Mar. 11, 2025

(54) DENTAL PANORAMIC VIEWS

(71) Applicant: Align Technology, Inc., San Jose, CA (US)

(72) Inventors: Maayan Moshe, Ramat Hasharon (IL); Shai Ayal, Tel Aviv (IL); Jonathan Coslovsky, Rehovot (IL); Adi Levin, Nes Tziona (IL); Avraham Zulti, Modiin (IL); Shai Farkash, Hod HaSharon (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 18/327,826

(22) Filed: Jun. 1, 2023

(65) Prior Publication Data

US 2023/0301611 A1    Sep. 28, 2023

Related U.S. Application Data

(63) Continuation of application No. 17/017,613, filed on Sep. 10, 2020, now Pat. No. 11,707,238.

(60) Provisional application No. 62/898,481, filed on Sep. 10, 2019, provisional application No. 62/991,532, filed on Mar. 18, 2020.

(51) Int. Cl.
| | |
|---|---|
| *A61B 6/51* | (2024.01) |
| *A61B 6/00* | (2006.01) |
| *A61B 6/46* | (2024.01) |
| *A61C 9/00* | (2006.01) |
| *A61N 5/10* | (2006.01) |

(52) U.S. Cl.
CPC .............. *A61B 6/51* (2024.01); *A61B 6/463* (2013.01); *A61B 6/465* (2013.01); *A61B 6/5211* (2013.01); *A61C 9/004* (2013.01); *A61N 5/103* (2013.01); *A61C 9/0053* (2013.01)

(58) Field of Classification Search
CPC ........... A61B 6/51; A61B 6/463; A61B 6/465; A61B 6/14; A61C 9/004; A61C 9/0053; A61N 5/103
See application file for complete search history.

(56) References Cited

U.S. PATENT DOCUMENTS

| | | | |
|---|---|---|---|
| 10,509,838 B2* | 12/2019 | Elbaz | A61C 1/088 |
| 10,643,107 B1* | 5/2020 | Yoo | G06F 18/253 |
| D925,739 S | 7/2021 | Shalev et al. | |
| 11,628,046 B2* | 4/2023 | Elbaz | A61B 1/00009 |
| | | | 433/29 |
| 11,707,238 B2 | 7/2023 | Moshe et al. | |
| RE49,605 E | 8/2023 | Kopelman | |
| 11,842,437 B2* | 12/2023 | Dibra | G06N 3/08 |
| 2012/0328071 A1* | 12/2012 | Katsumata | A61B 6/51 |
| | | | 378/4 |

(Continued)

FOREIGN PATENT DOCUMENTS

CN    105934201 A    9/2016

*Primary Examiner* — Nicholas D Lucchesi
(74) *Attorney, Agent, or Firm* — Shay Glenn LLP

(57) ABSTRACT

Provided herein are devices and methods generating synthetic views of a subject's teeth. Methods and processes are provided to image the subject's teeth with a dental scan. Methods and processes are also provided to automatically 3D render the subject's teeth with the scan images. Methods and apparatuses are also provided to generate simulated synthetic views of the subject's dentition from various perspectives.

20 Claims, 24 Drawing Sheets

(56) References Cited

U.S. PATENT DOCUMENTS

| | | | | |
|---|---|---|---|---|
| 2015/0004558 A1* | 1/2015 | Inglese | ................ | A61B 6/4233 |
| | | | | 433/29 |
| 2018/0028065 A1* | 2/2018 | Elbaz | .................... | A61B 5/7435 |
| 2018/0174367 A1* | 6/2018 | Marom | ................ | G06T 19/006 |
| 2019/0029522 A1* | 1/2019 | Sato | ...................... | A61B 5/4848 |
| 2019/0102880 A1* | 4/2019 | Parpara | .................... | B29C 51/46 |
| 2019/0231492 A1* | 8/2019 | Sabina | ............... | A61B 1/00172 |
| 2019/0254783 A1* | 8/2019 | Moon | ................ | A61B 1/00045 |
| 2020/0268339 A1* | 8/2020 | Hao | ...................... | G06T 7/0014 |
| 2020/0364624 A1* | 11/2020 | Kearney | ............... | G06F 18/256 |
| 2020/0405242 A1* | 12/2020 | Kearney | ................ | G06N 3/088 |
| 2020/0411167 A1* | 12/2020 | Kearney | .................. | G06T 7/77 |
| 2021/0059796 A1* | 3/2021 | Weiss | .................... | A61C 9/0053 |
| 2021/0068773 A1* | 3/2021 | Moshe | ...................... | A61B 6/51 |
| 2021/0128281 A1 | 5/2021 | Peleg | | |
| 2021/0137653 A1 | 5/2021 | Saphier et al. | | |
| 2021/0196152 A1 | 7/2021 | Saphier et al. | | |
| 2021/0358123 A1* | 11/2021 | Kearney | ................ | G16H 30/40 |
| 2022/0012888 A1* | 1/2022 | Chen | ........................ | G06T 5/30 |
| 2022/0083807 A1* | 3/2022 | Zhang | .................... | G06N 3/084 |
| 2022/0215531 A1* | 7/2022 | Azernikov | ................ | G06T 7/11 |
| 2023/0009661 A1* | 1/2023 | Sarti | .................... | G06T 3/4038 |
| 2023/0068727 A1* | 3/2023 | Saphier | ..................... | G06T 7/70 |
| 2024/0058105 A1* | 2/2024 | Saphier | ................ | G06T 17/00 |
| 2024/0115196 A1* | 4/2024 | Moshe | ................ | A61B 5/4552 |
| 2024/0144480 A1* | 5/2024 | Seeber | ..................... | G06T 5/10 |

\* cited by examiner

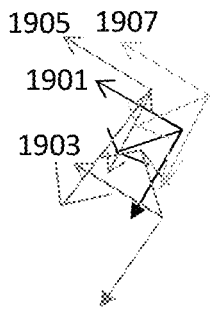
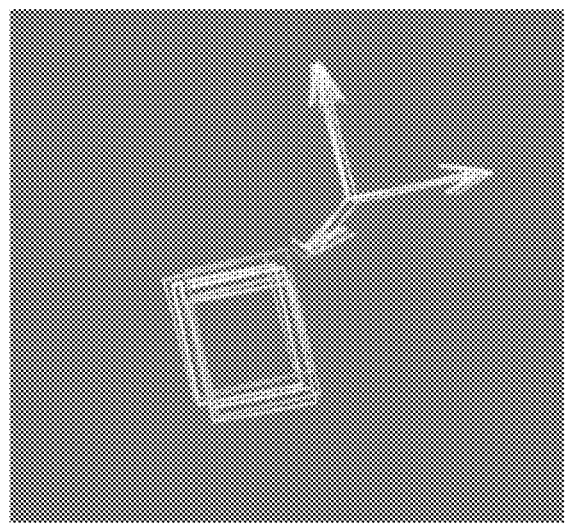
FIG. 19  FIG. 20
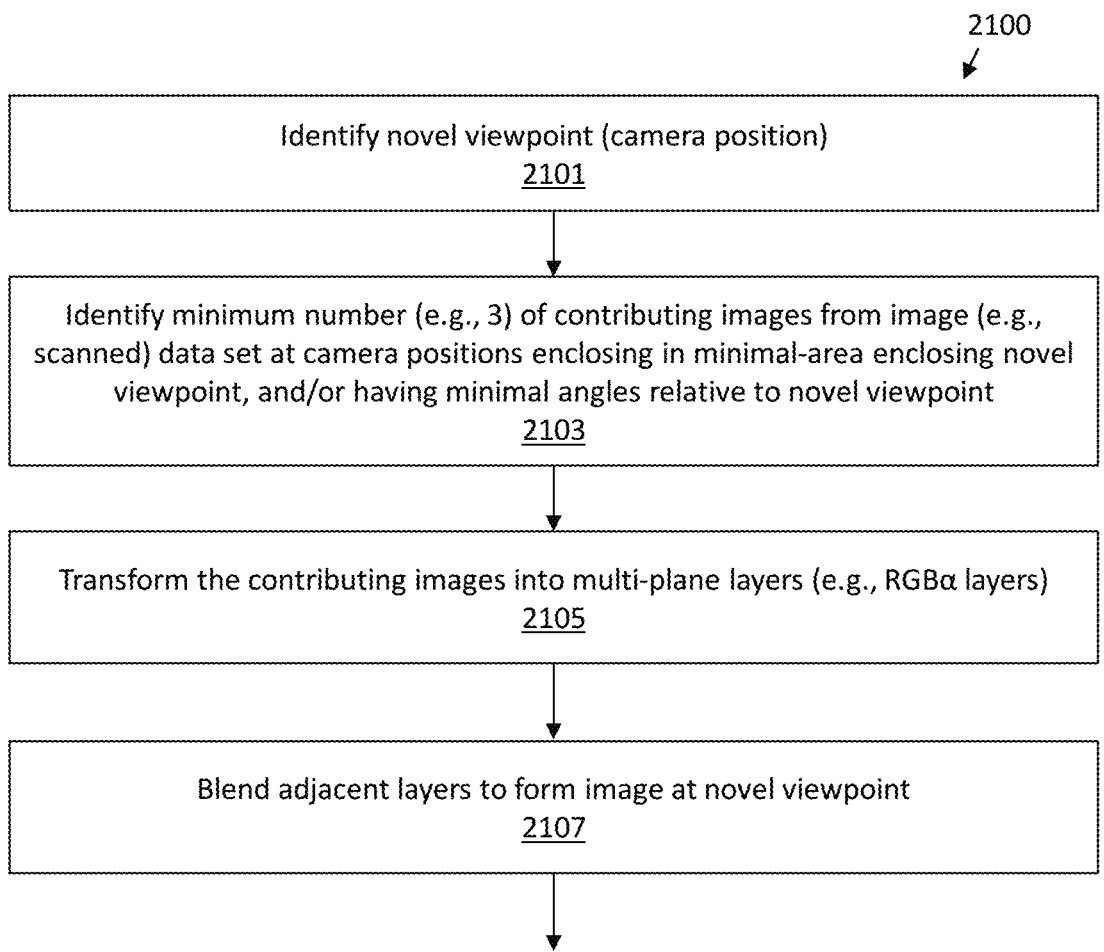
FIG. 21

Predicted

Ground truth

Predicted

Ground truth

DENTAL PANORAMIC VIEWS

CLAIM OF PRIORITY

This patent application is a continuation of U.S. patent application Ser. No. 17/017,613, filed Sep. 10, 2020, titled "DENTAL PANORAMIC VIEWS," now U.S. patent No. 11,707,238, which claims priority to U.S. Provisional Patent Application No. 62/898,481, filed Sep. 10, 2019, titled "3D SCREEN VIEW FROM MULTIPLE PANORAMIC VIEWS," and U.S. Provisional Patent Application No. 62/991,532, filed Mar. 18, 2020, titled "3D SCREEN VIEW FROM MULTIPLE PANORAMIC VIEWS," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Many dental and orthodontic procedures can benefit from accurate three-dimensional (3D) descriptions of a patient's dentation and intraoral cavity. Surface representations of the 3D surfaces of teeth have proven extremely useful in the design and fabrication of dental prostheses (e.g., crowns or bridges), and treatment plans.

Historically, ionizing radiation (e.g., X-rays) have been used to image into the teeth. For example, X-Ray bitewing radiograms are often used to provide non-quantitative images into the teeth. However, in addition to the risk of ionizing radiation, such images are typically limited in their ability to show features and may involve a lengthy and expensive procedure to take. Other techniques, such as cone beam computed tomography (CBCT) may provide tomographic images, but still require ionizing radiation.

Specialized 3D scanning tools have also been used to image teeth. Scans from the 3D scanning tools provide topographical data of a patient's dentation that can be used to generate a 3D dental mesh model of the patient's teeth. The 3D dental mesh models may comprise polyhedral objects that depict teeth and/or other elements of the dental arch in a format that can be rendered on a display. However, generating 3D dental mesh models can be very time consuming and processor intensive to generate, and can result in low resolution, low detail 3D models that do not accurately and realistically visualize the surface of a patient's teeth.

Thus, it would be beneficial to provide methods and apparatuses, including devices and systems, such as intraoral scanning systems, that may be used to accurately and efficiently provide high-resolution, photo-realistic models of a patient's teeth. There is a need for improved methods and systems for scanning an intraoral cavity of a patient, and/or for visualizing the patient's teeth.

SUMMARY

In general, described herein are methods and apparatuses (e.g., devices and systems) for scanning and visualizing a patient's dental arch and teeth. These methods and apparatuses may generate a photo-realistic color or grayscale renderings of a subject's teeth. Any of these apparatuses may include cameras or intraoral scanners for scanning into or around a subject's oral cavity. The scanning apparatus may also include one or more sensors for detecting a precise location of the scanning apparatus during the scan. The generated model may be a panoramic image. The panoramic image may be referred to herein as a 3D rendering or may be used to generate a 3D rendering. These panoramic views may be generated instead of, or in addition to, a three-dimensional volumetric model of the teeth, which may include internal structures of the teeth.

The use of panoramic images as described herein to display views of all or portions of a patient's dentition (e.g., upper and/or lower dental arch), in which input scan images, such as intraoral scan images, may provide many advantages as compared to other described methods in which the scanned images are shown piecemeal or as a synthesized 3D (e.g., digital) model. Piecemeal, or even collaged images are not satisfactorily smooth and may show abrupt and jarring transitions and changes in orientation, including introduced artifacts. Synthesized (e.g., digital 3D) models may also be computationally- and time-consuming, and may be particularly difficult to accurately represent color, transparency, light effects, and internal structures. Such techniques also require (and may introduce artifacts due to) segmentation.

The methods and apparatuses described herein may avoid these difficulties and may provide quick and realistic images that may be viewed at arbitrary zoom and position. The panoramic images described herein may be shown in real time, and may provide continuous, smooth transition between different panoramic views, allowing for continuous, real-time viewing, rotation, pan, zoom, etc.

The methods described herein typically include methods for generating a 3D rendering of a subject's teeth with a panoramic image or images of the teeth that include surface or internal features. In particular, multiple images of the subject's teeth may be taken from the multiple positions. Position data of the camera can be recorded during image acquisition and the images can be blended together using the position data.

The methods and systems described herein may be used to generate a 2D image and/or 3D rendering showing internal features of a subject's teeth, surface features of the subject's teeth, or both. The different internal and surface features may be visualized using data collected using one or more scanning modalities of the intraoral scanner. For example, the 2D and 3D renderings may be generated using data collected using an infrared (IR) light, visible light, or combination thereof. In some cases, the data acquired from the intraoral scanner is combined with other image data.

The methods and systems described herein may be used to generate simulated views (e.g., bitewing views) based on selected images taken from one or more predetermined camera angles (positions and/or orientations) during one or more scanning operations of the subject's teeth. Such methods can include determining a center jaw line is determined and identifying camera angles for those images in the scan data corresponding to a selected viewing angle for generating the view.

The methods and systems described herein can enable a user to select a particular perspective for viewing the subject's teeth. For example, the user can select to view the dentition from above or below to visualize an occlusal view of the dental arch, from a lingual perspective, and/or from a buccal perspective. In some instances, the user may rotate the images to update the various views.

For example, described herein are methods of displaying a panoramic view of a dental arch. These methods may include: receiving a plurality of two-dimensional (2D) infrared images of the dental arch each taken at an associated camera angle; identifying a viewing angle for viewing the panoramic view of the dental arch; identifying a center jaw line for the plurality of 2D images and identifying a plurality of points along the center jaw line; generating the panoramic view at the viewing angle from the center jaw line and the plurality of points, and displaying the panoramic view. Generating the panoramic view at the viewing angle from the center jaw line and the plurality of points may include selecting, for each point of the plurality of points, an image that is based on one or more 2D images from the plurality of 2D images that includes the point and has a camera angle that corresponds to the viewing angle; and combining the selected images.

Identifying the center jaw line for the plurality of 2D images may include arranging the plurality of 2D images along the center jaw line based on one or more of: a content of the 2D images and position information collected for each 2D image when the 2D image was taken.

Combining may comprise combining along a line corresponding to the center jaw line. In general, the center jaw line may be any line that extends through the plurality of 2D images. The center jaw line may approximately correspond to the path taken by an intraoral scanner taking the images relative to the dental arch. The center jaw line (which may be referred to for simplicity as a trace line) may be curved, straight, or any other shape. The center jaw line may be wrapped or not wrapped. The center jaw line does not have to be absolutely centered (e.g., on the tooth), but may be approximately centered.

The points may be pixels (or groups of pixels) on the images. In some variations, the points may be virtual pixels on a virtual screen, e.g., through a centerline identified from the scanned dental arch.

In any of these apparatuses and methods, combining the selected images, e.g., when arranging in the panoramic view, may include comprises blending the selected images to match gradients at boundaries of adjacent selected images. Generating the panoramic view may include displaying the teeth of the dental arch in a line in accordance with a linear center jaw line.

In any of these methods and apparatuses, the user may select and/or change, including dynamically selecting and/or changing, the viewing angle for the panoramic view. For example, changing the viewing angle to a second (or other) viewing angle may be based on a user input, and any of these methods and apparatuses may include generating a second panoramic view using the second viewing angle. The original (e.g., first) viewing angle may be selected or set by the user interface. The user interface may allow the user to rotate or otherwise move (translate, including rotation) the panoramic view or another representation of the dental arch. Thus, the viewing angle may be chosen by a user via a user interface that allows the user to move the panoramic view. In some variations, the user interface may display the panoramic view and may include one or more tools to allow the user to interactive and (e.g., in real time) manipulate the view(s). In some variations, the viewing angle (e.g., the initial viewing angle) may be perpendicular to a virtual screen passing through the center jaw line.

Any of these methods and apparatuses may include rendering regions of the panoramic view having different densities or compositions with different shades or colors.

As will be described in greater detail, any of these methods and apparatuses may be used to help plan/create, modify or track a treatment plan, such as an orthodontic treatment plan. These methods may, for example, allow for comparison between a patient's actual dental arch (e.g., showing actual tooth positions) and a predicted (e.g., digitally modeled) dental arch, showing predicted tooth position. The panoramic views of the actual and virtual (digitally modeled) dental arches may be compared. In some variations, these methods and apparatuses may be used to create a treatment plan based on the panoramic view, and/or may be used for implementing the treatment plan on the patient.

Amy of these methods and apparatuses may include forming one or more dental appliances in accordance with a treatment plan based on the panoramic view.

Further, in some variations the method may include a step of scanning a patient's dental arch to collect the plurality of two-dimensional (2D) images (e.g., IR images, such as near-IR images) of the dental arch may be received from a separate (remote in time or location) intraoral scanner.

The step of selecting, for each point of the plurality of points, the image that is based on one or more 2D images from the plurality of 2D images comprises selecting the image from the one or more 2D images from the plurality of 2D images that has a camera angle that most closely approximates the viewing angle. Alternatively or additionally, in some variations, selecting, for each point of the plurality of points, the image that is based on one or more 2D images from the plurality of 2D images may comprise extrapolating an image from the one or more 2D images.

Also described herein are apparatuses, including systems, configured to perform any of these methods. For example, described herein are systems comprising: one or more processors; and a memory coupled to the one or more processors, the memory comprising a non-transitory computing device readable medium having instructions stored thereon that are executable by the one or more processors to perform a method comprising: receiving a plurality of two-dimensional (2D) infrared images of the dental arch each taken at an associated camera angle; identifying a viewing angle for viewing the panoramic view of the dental arch; identifying a center jaw line for the plurality of 2D images and identifying a plurality of points along the center jaw line; generating the panoramic view at the viewing angle by: selecting, for each point of the plurality of points, an image that is based on one or more 2D images from the plurality of 2D images that includes the point and has a camera angle that corresponds to the viewing angle; and combining the selected images; and displaying the panoramic view. The instructions may further comprise identifying the viewing angle by receiving the viewing angle from a user interface. The user interface may be configured to allow a user to dynamically change the viewing angle and to display the corresponding panoramic view.

Also described herein are methods of displaying a dental arch, the method comprising: receiving a plurality of two-dimensional (2D) images of the dental arch each taken at an associated camera angle, wherein the plurality of 2D images includes internal features of teeth of the dental arch; aggregating the plurality of 2D images to generate a panoramic view of the dental arch along a center jaw line; passing a virtual plane through the panoramic view at a specified height and angle with respect to the center jaw line; and generating a 2D slice view based on the specified height and angle, the slice view including corresponding internal features of the teeth. Any of these methods may also include passing a second virtual plane through the panoramic view at a second specified height and angle with respect to the center jaw line, and generating a second 2D slice view.

The 2D slice view may include different shading or colors for areas of the dental arch having different densities or compositions.

Any of these methods may include passing a plurality of virtual planes through the panoramic view at different specified heights and at the same angle with respect to the reference plane, and generating a plurality of 2D slice views based on the plurality of virtual planes. These methods may also include displaying the plurality of 2D slice views in an animation showing progression through the dental arch. The plurality of 2D images may include images collected using a near infrared light source. The plurality of 2D images may further include images collected using a visible light source.

Any of these methods may also include creating a treatment plan based at least in part on the 2D slice view, and in some variations implementing a treatment plan on the patient. Any of these methods may also or alternatively include: creating a treatment plan based at least in part on the 2D slice view; and fabricating one or more orthodontic devices based on the treatment plan.

Also described herein are non-transitory computing devices readable medium having instructions stored thereon that are executable by a processor to cause a computing device to perform a method comprising: receiving a plurality of two-dimensional (2D) images of the dental arch each taken at an associated camera angle, wherein the plurality of 2D images includes internal features of teeth of the dental arch; aggregating the plurality of 2D images to generate a panoramic view of the dental arch along a center jaw line; passing a virtual plane through the panoramic view at a position with respect to the center jaw line; and generating a 2D slice view based on the specified position, the 2D slice view including corresponding internal features of the teeth.

A method of displaying a dental arch may include: receiving a plurality of two-dimensional (2D) images of the dental arch each taken at an associated camera angle, wherein the plurality of 2D images includes internal features of teeth of the dental arch; aggregating the plurality of 2D images to generate a panoramic view of the dental arch at a viewing angle from a center jaw line through the dental arch; identifying a region of interest within the panoramic view, the region of interest corresponding to a volume at a specified location of the panoramic view; and rendering the panoramic view on a display such that at least a portion of the region of interest is partially transparent to show corresponding internal features within the region of interest. The plurality of 2D images may include images collected using a near infrared light source. The plurality of 2D images may further include images collected using a visible light source. In some variations, identifying the region of interest includes automatically identifying the region of interest based on density or composition. Identifying the region of interest may include receiving input from a user that identifies the specified location. Rendering the panoramic view may include rendering different internal features within the region of interest with different shades or colors.

Any of these methods may also or alternatively include creating a treatment plan based at least in part on the rendered panoramic view; and implementing the treatment plan on the patient. In some variations, these methods may include creating a treatment plan based at least in part on the rendered panoramic view; and fabricating one or more orthodontic devices based on the treatment plan.

Also described herein are non-transitory computing device readable mediums having instructions stored thereon that are executable by a processor to cause a computing device to perform a method comprising: receiving a plurality of two-dimensional (2D) images of the dental arch each taken at an associated camera angle, wherein the plurality of 2D images includes internal features of teeth of the dental arch; aggregating the plurality of 2D images to generate a panoramic view of the dental arch at a viewing angle from a center jaw line through the dental arch; identifying a region of interest within the panoramic view, the region of interest corresponding to a volume at a specified location of the panoramic view; and rendering the panoramic view on a display such that at least a portion of the region of interest is partially transparent to show corresponding internal features within the region of interest.

Methods and apparatuses for forming a novel, synthesized image at a selected viewpoint are also described. These methods may be used to generate a panoramic view, as described herein.

For example, described herein are methods of generating a novel view from a plurality of intraoral scanning views. These methods may include: receiving a plurality of two-dimensional (2D) images of a dental arch each taken at an associated camera angle and position; identifying a novel viewpoint having a camera angle and position relative to the dental arch; identifying three or more contributing images from the plurality of 2D images, wherein the contributing images have a minimal angle relative to camera angle of the novel viewpoint and wherein the camera position of the novel viewpoint is bounded by a triangle formed by the camera positions of the three or more contributing images; transforming the contributing images into multi-plane layers; blending the adjacent multiplane layers of the contributing images to form the novel view; and displaying all or a portion of the novel view. Any of these methods may also include identifying the novel viewpoint by camera position and orientation.

In some variations, exactly three contributing images may be used. The plurality of two-dimensional (2D) images of the dental arch may be received from data taken by an intraoral scanner. This data may be accessed, read or otherwise received.

Identifying the novel viewpoint may include identifying a point (and camera angle/direction) taken from a user interface (e.g., by user input), and/or identifying the viewpoint and camera angle as part of a panoramic view generating method. The three or more contributing images may be identified after confirming that the intersection over union for each of the three or more contributing images is greater than 0.5. If the intersection over union is not greater than 0.5 a different contributing image may be used.

The contributing images may have a minimal angle relative to camera angle of the novel viewpoint that is x degrees or less (e.g., 15 degrees or less, 12 degrees or less, 10 degrees or less, 8 degrees or less, 6 degrees or less, 5 degrees or less, 4 degrees or less, 3 degrees or less, 2 degrees or less, 1 degree or less, etc.). In some variations the camera angle of the contributing images is approximately the same as the camera angle of the novel viewpoint.

The method wherein blending comprises applying a trained machine learning agent to blend the adjacent multi-plane layers of the contributing images to form the novel view. The machine learning agent may be trained on a plurality of intraoral scanning views.

Also described herein are non-transitory computing device readable medium having instructions stored thereon that are executable by a processor to cause a computing device to perform any of these methods, including the method of generating a novel view from a plurality of intraoral scanning views, such as: receiving a plurality of two-dimensional (2D) images of a dental arch each taken at an associated camera angle and position; identifying a novel viewpoint having a camera angle and position relative to the dental arch; identifying three or more contributing images from the plurality of 2D images, wherein the contributing images have a minimal angle relative to camera angle of the novel viewpoint and wherein the camera position of the novel viewpoint is bounded by a triangle formed by the camera positions of the three or more contributing images; transforming the contributing images into multi-plane layers; blending the adjacent multiplane layers of the contributing images to form the novel view; and displaying all or a portion of the novel view.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 17A illustrates an example of a dental arch shown in a 3D projection, and surrounded by a cylindrical "screen" on the lingual, occlusal and buccal sides of a dental arch. FIG. 17B shows an occlusal view of the same dental arch shown in FIG. 17A, with a section through the dental arch showing the surrounding "screen". FIG. 17C shows the sectional view through the section indicated in FIG. 17B, providing a cross-section of the tooth and the surrounding screen.

FIG. 18A shows a normal occlusal view of a dental arch; FIG. 18B illustrates an example of a cylindrical projection of the same dental arch shown in FIG. 18A.

FIG. 19 illustrates one example of the selection of a novel view camera direction (shown in black) as compared to the camera directions of three surrounding contributing images that may be used to generate the novel view.

FIG. 20 illustrates the intersection over union of three contributing images as compared to the novel view and the ground state, showing an intersection over union of greater than 0.5.

FIG. 21 illustrates one example of a method of determining a novel, synthesized image from a plurality of scanned images.

FIGS. 22A-22C show three contributing images identified as having a minimal camera angle relative to the camera angle of the novel viewpoint (e.g., approximately the same camera direction) in which the novel camera position is within a triangle formed by the camera positions of images from the dataset having a minimal volume as compared to other triangles formed from the camera positions of images also having approximately the same camera angle. FIG. 22D shows the predicted novel, synthesized image and FIG. 22E shows the ground truth image for the novel viewpoint.

FIGS. 23A-23C show three contributing images identified as having a minimal camera angle relative to the camera angle of the novel viewpoint (e.g., approximately the same camera direction) in which the novel camera position is within a triangle formed by the camera positions of images from the dataset having a minimal volume as compared to other triangles formed from the camera positions of images also having approximately the same camera angle. FIG. 23D shows the predicted novel, synthesized image and FIG. 23E shows the ground truth image for the novel viewpoint.

DETAILED DESCRIPTION

Figure 1A:
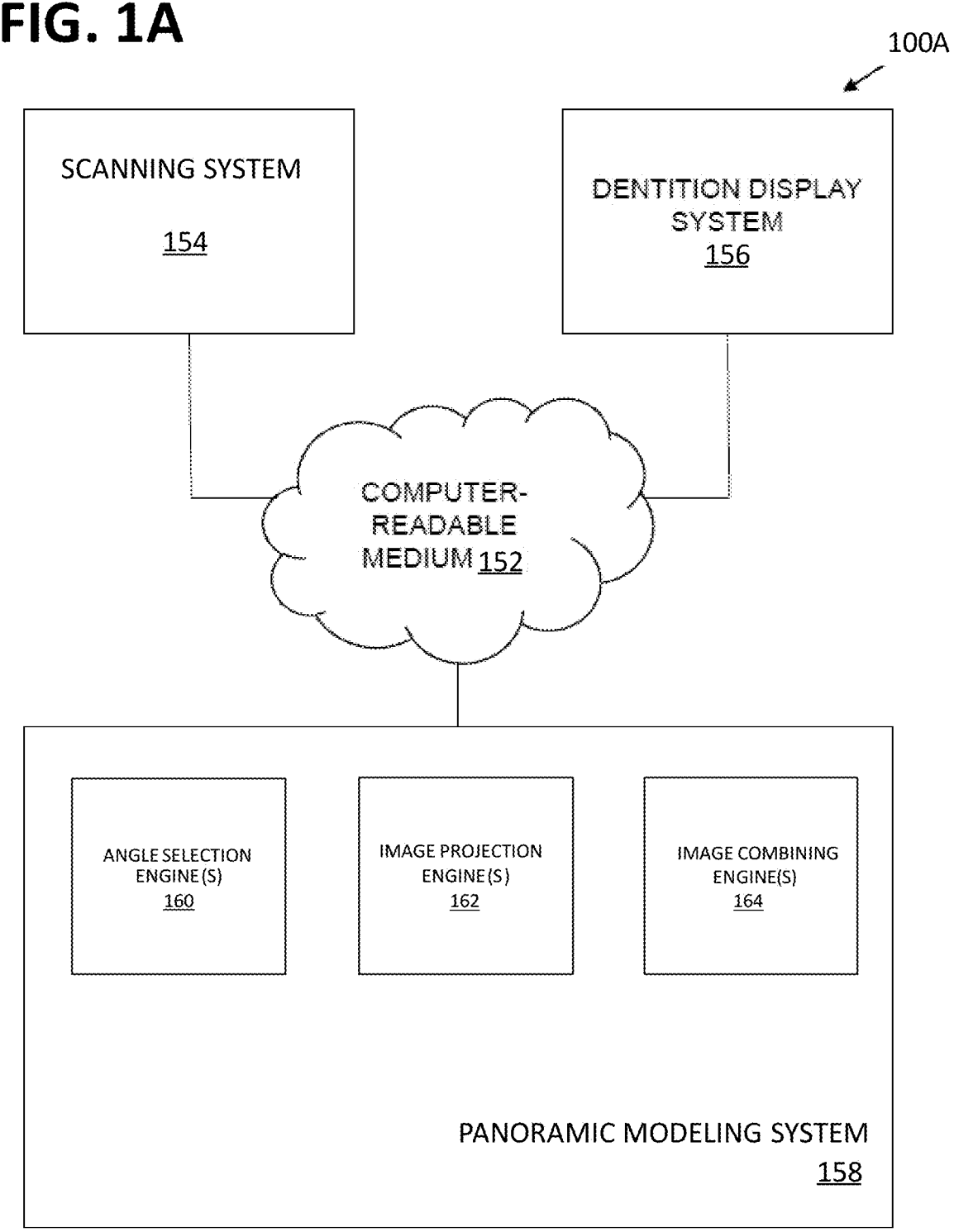
FIG. 1A is a diagram showing an example of a computing environment configured to generate a panoramic model of a subject's teeth.

The present disclosure is related to systems, methods, computing device readable media, and devices for generating a model of a subject's intraoral region (e.g., tooth or teeth, gums, jaw, etc.). The systems, methods, and computing devices herein solve technical problems related to design and display of models of a patient's arch, including quickly and efficiently displaying a photo-realistic image or model of the surface of a subject's teeth.

Described herein are scanning or camera systems for generating photo-realistic images of a subject's intraoral region including external or surface features of the teeth, or internal features of the teeth, and methods of using such scanning or camera systems. An intraoral scanner or camera system may include a wand that can be hand-held by an operator (e.g., dentist, dental hygienist, technician, etc.) and moved over a subject's tooth or teeth to scan surface structures of the subject's teeth. The wand may include one or more detectors (e.g., cameras such as CMOS, CCDs, etc.), one or more light sources (visible light, infra-red light) and one or more sensors (e.g., accelerometers, GPS, etc.) for measuring and recording the position and/or orientation of the intraoral scanner or camera system during image acquisition. Specifically, the intraoral scanner or camera system can be configured to measure and record the precise position and orientation of the camera as images are captured, and can further be configured to associate the position and orientation of the camera with each image taken at that position and orientation. The wand may include one or more controls (buttons, switching, dials, touchscreens, etc.) to aid in control (e.g., turning the wand on/of, etc.); alternatively or additionally, one or more controls, may be present on other parts of the intraoral scanner, such as a foot petal, keyboard, console, touchscreen, etc.

The dental models produced with intraoral scanners and camera systems, as described herein, can be used in the planning and fabrication of dental appliances, including elastic polymeric positioning appliances, as described in detail in U.S. Pat. No. 5,975,893, and in published PCT application WO 98/58596, which are herein incorporated by reference for all purposes. Systems of dental appliances employing technology described in U.S. Pat. No. 5,975,893 are commercially available from Align Technology, Inc., San Jose, Calif., under the tradename, Invisalign System. It may also be used to aid in dental diagnosis, for example diagnosis of dental caries and/or diagnosis of gingival pockets.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

As described herein, an intraoral scanner or camera system may image a patient's dental arch and generate a virtual model of that dental arch. In some examples, the model can be a three-dimensional (3D) model of the dental arch. During an intraoral scan procedure (also referred to as a scan session), a user (e.g., a dental practitioner) of an intraoral scanner or camera system may generate multiple different images (also referred to as scans or medical images) of a dental site, model of a dental site, or other object. The images may be discrete images (e.g., point-and-shoot images) or frames from a video (e.g., a continuous scan). The images may be taken in the visible light or in infra-red (IR) light (e.g., pure or near IR light) or other wavelengths. The intraoral scanner may automatically generate a model of the patient's teeth from the images, which can be used for treatment planning.

FIG. 1A is a diagram showing an example of a computing environment 100A configured to digitally scan a dental arch of a subject. The environment 100A includes a computer-readable medium 152, a scanning system 154, a dentition display system 156, and a panoramic modeling system 158. One or more of the modules in the computing environment 100A may be coupled to one another or to modules not explicitly shown.

The computer-readable medium 152 and other computer readable media discussed in this disclosure are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to capture still images, video, and/or other media of a patient's dental arch. The scanning system 154 may include memory, one or more processors, and sensors to detect contours on a patient's dental arch. The scanning system 154 may further include sensors configured to measure and/or record a position and orientation of the scanning system during image acquisition. The scanning system 154 may be implemented as a camera, an intraoral scanner, an x-ray device, an infrared device, etc. The scanning system 154 may include a system configured to provide a virtual representation of a mold of patient's dental arch. A "dental arch," as used herein, may include at least a portion of a patient's dentition formed by the patient's maxillary or mandibular teeth, when viewed from an occlusal perspective. A dental arch may include one or more maxillary or mandibular teeth of a patient, such as all teeth on the maxilla or mandible or a patient. The scanning system 154 may be used as part of an orthodontic treatment plan. In some implementations, the scanning system 154 is configured to capture a patient's dental arch at a beginning stage, an intermediate stage, etc. of an orthodontic treatment plan.

The dentition display system 156 may include a computer system configured to display at least a portion of a dentition of a patient. The dentition display system 154 may include memory, one or more processors, and a display device to display the patient's dentition. The dentition display system 156 may be implemented as part of a computer system, a display of a dedicated intraoral scanner, etc. In some implementations, the dentition display system 156 facilitates display of a patient's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include virtual representations or models of the dental arch, 2D images or renditions of the dental arch, 2D or 3D panoramic images or models of the dental arch, etc.

The panoramic modeling system 158 may include a computer system configured to process scans or images of a patient's dentition taken by the scanning system 154. The panoramic modeling system 158 may include angle selection engine(s) 160, image projection engine(s) 162, and image combining engine(s) 164. One or more of the modules of the panoramic modeling system may be coupled to each other or to modules not shown.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The angle selection engine(s) 160 may implement one or more automated agents configured to identify the key camera angles for which to construct the panoramic model. In some implementations, the angle selection engine(s) 160 is configured to generate a sphere (or at least a portion of a sphere) that represents the panoramic model. The angle selection engine(s) 160 can be further configured to triangulate the sphere (or at least a portion of the sphere) into a plurality of triangles, with the vertices of each triangle representing a key camera angle required for building the panoramic model. The angle selection engine(s) 160 may provide key camera angles and/or other data to other modules of the panoramic modeling system 158.

The image projection engine(s) 162 may implement one or more automated agents configured to project images from the scan of the subject's teeth to form an initial panoramic model for each key camera angle. The image projection engine(s) 162 may receive images and camera position and/or orientation data from the scanning system 154. In some implementations, the image projection engine(s) 162 is configured to form a two-dimensional grid of points that includes all the pixel positions needed to construct the panoramic model for a given key camera angle. In one implementation, a two-dimensional grid can be formed by dividing the center jaw line into equidistant segments, forming a line at each segment, and identifying the equidistant points on each line. The lines can be perpendicular to the center jaw line and to the each key camera angle. The point cloud of all camera positions and orientations recorded during the scan can be compared to the points on each line, and the image projection engine(s) 162 can be configured to select the physical camera locations most suitable, for example the camera with orientation closest to the key camera angle for each point of each line. The most suitable image for each point of the two-dimensional grid can be approximated with an orthographic camera to provide images for each of the points of each line, resulting in an initial panoramic model for each key camera angle. Alternatively, other images selection criteria may be employed. The image projection engine(s) 162 may provide the two-dimensional grid of points, the projected images, the initial panoramic model, and/or other data to other modules of the panoramic modeling system 158.

The image combining engine(s) 164 may implement one or more automated agents configured to register, deform, and/or blend the images of the initial panoramic model to create the final panoramic model for each key camera angle. In some implementations, the image combining engine(s) 164 is configured to register and/or deform the images in the initial panoramic model to match gradients at the boundaries of adjacent images. The image combining engine(s) 164 may be further configured to blend the resulting images to produce a final panoramic model for each key camera angle. Additionally, the image combining engine 164 may be configured to render the final panoramic model to the user for a chosen key camera angle.

Figure 1B:
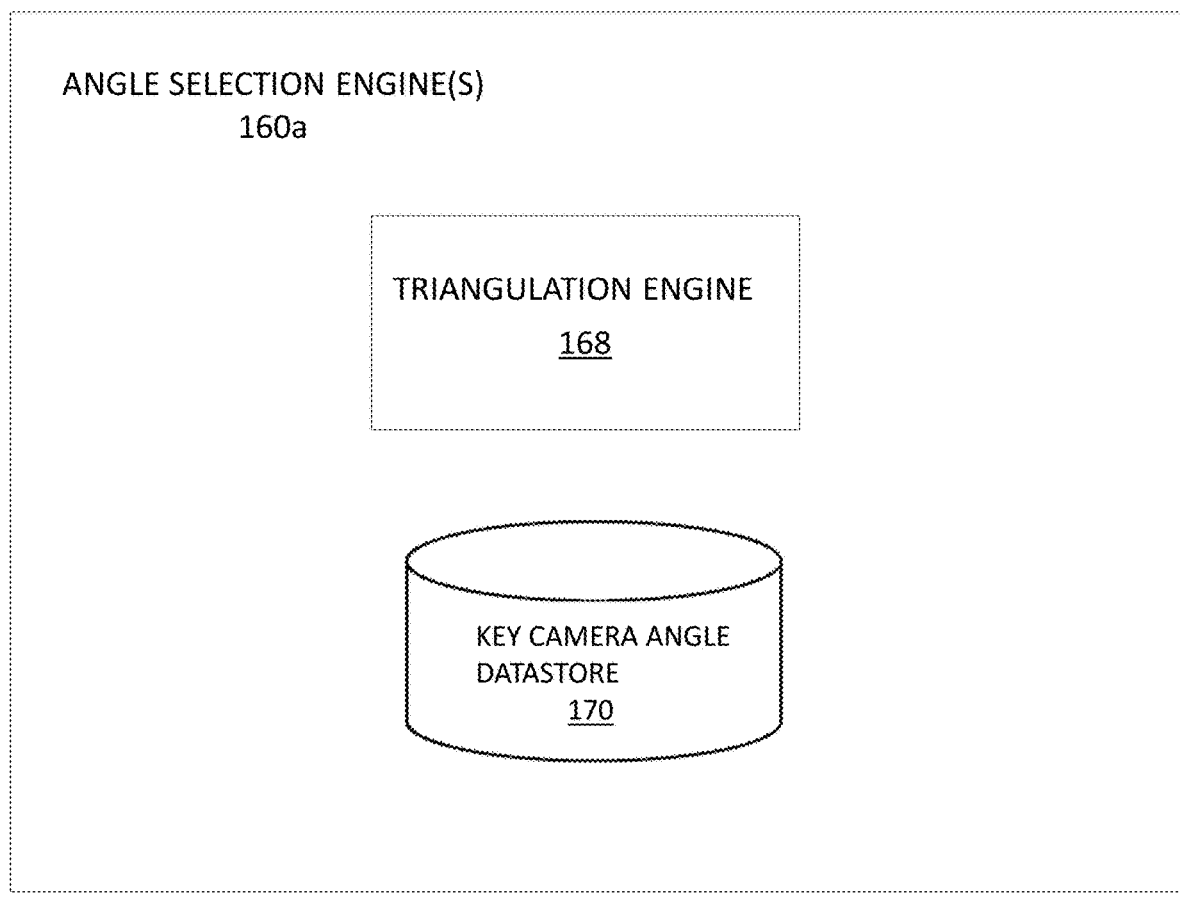
FIG. 1B is a diagram showing an example of angle selection engine(s).

FIG. 1B is a diagram showing an example of an angle selection engine(s) 160*a*. The angle selection engine(s) 160*a* may include a triangulation engine 168 and a key camera angle datastore 170. One or more of the modules of angle selection engine(s) 160*a* may be coupled to each other or to modules not shown.

The triangulation engine 168 may implement one or more automated agents configured to identify the key camera angles for which to construct the panoramic model. In some implementations, the triangulation engine 168 triangulates a sphere or part of a sphere into a plurality of triangles, and identifies vectors originating at coordinate 0 of the sphere or part of a sphere and ending at each vertex of the plurality of triangles as being the key camera angles required for building the panoramic model.

The key camera angle datastore 170 may be configured to store data related to the key camera angles identified by the triangulation engine. The key camera angle data may comprise a matrix of camera angles and/or positions required to generate a panoramic model of the subject's teeth.

Figure 1C:
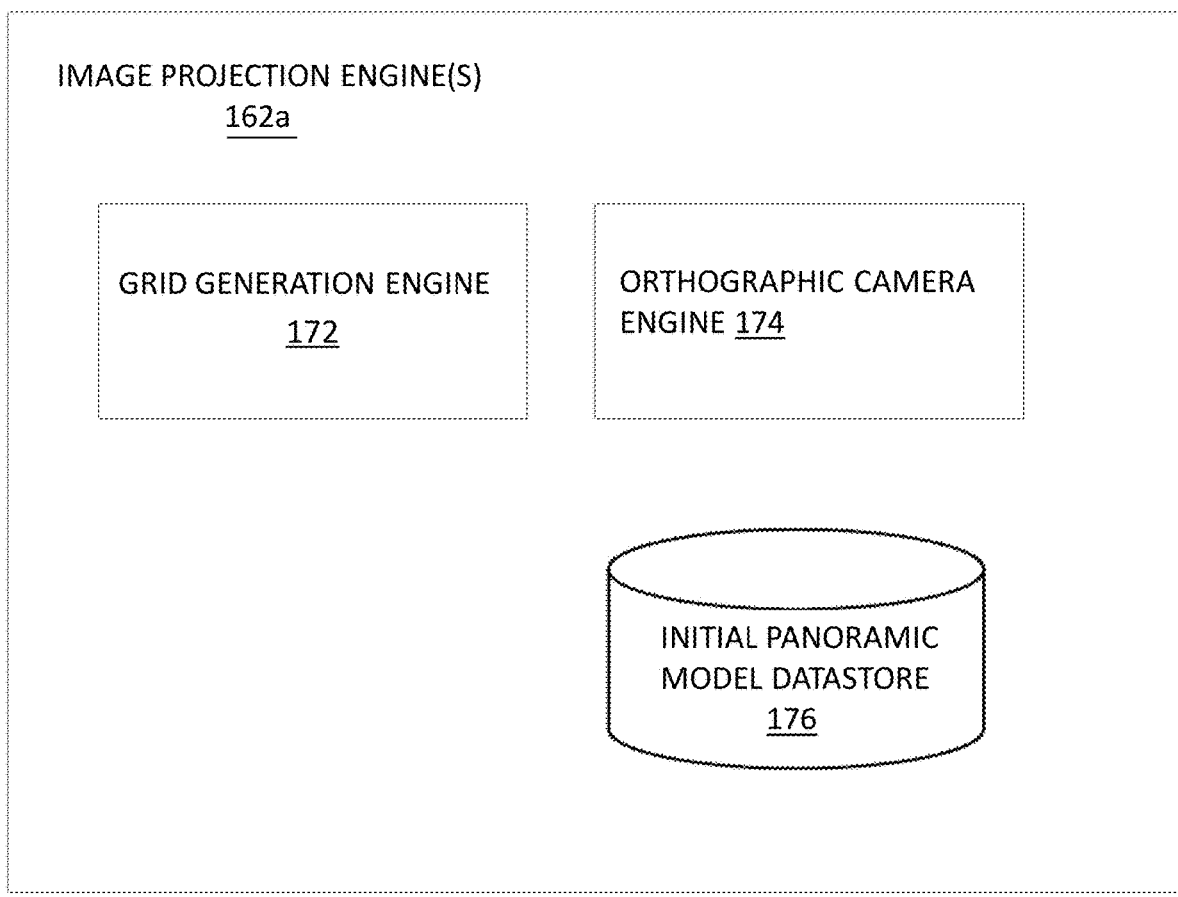
FIG. 1C is a diagram showing an example of image projection engine(s).

FIG. 1C is a diagram showing an example of an image projection engine(s) 162a. The image projection engine(s) 162a may include a grid generation engine 172, an orthographic camera engine 174, and an initial panoramic model datastore 176. One or more of the modules of the image projection engine(s) 162a may be coupled to each other or to modules not shown.

The grid generation engine 172 may implement one or more automated agents configured to form a two-dimensional grid of points representing the images and camera positions required to generate the panoramic model. In one implementation, the two-dimensional grid can be formed by dividing the center jaw line of the subject into equidistant segments and forming lines at each segment. The lines can be perpendicular to the center jaw line and to the each key camera angle. Furthermore, the grid generation engine can be configured to index points along each line to form the two-dimensional grid of points.

The orthographic camera engine 174 may implement one or more automated agents configured to approximate images at the points in the two-dimensional grid of points with the images from the scan that most suitable, for example the camera with orientation closest to the key camera angle to the desired point positions. The combination of all the approximated images at each of the points in the two-dimensional grid of points results in the generation of an initial panoramic model of the subject's teeth for each key camera angle.

The initial panoramic model datastore 176 may be configured to store data related to the two-dimensional grid of points generated by the grid generation engine, and to store data related to the initial panoramic model generated by the orthographic camera engine 174.

Figure 1D:
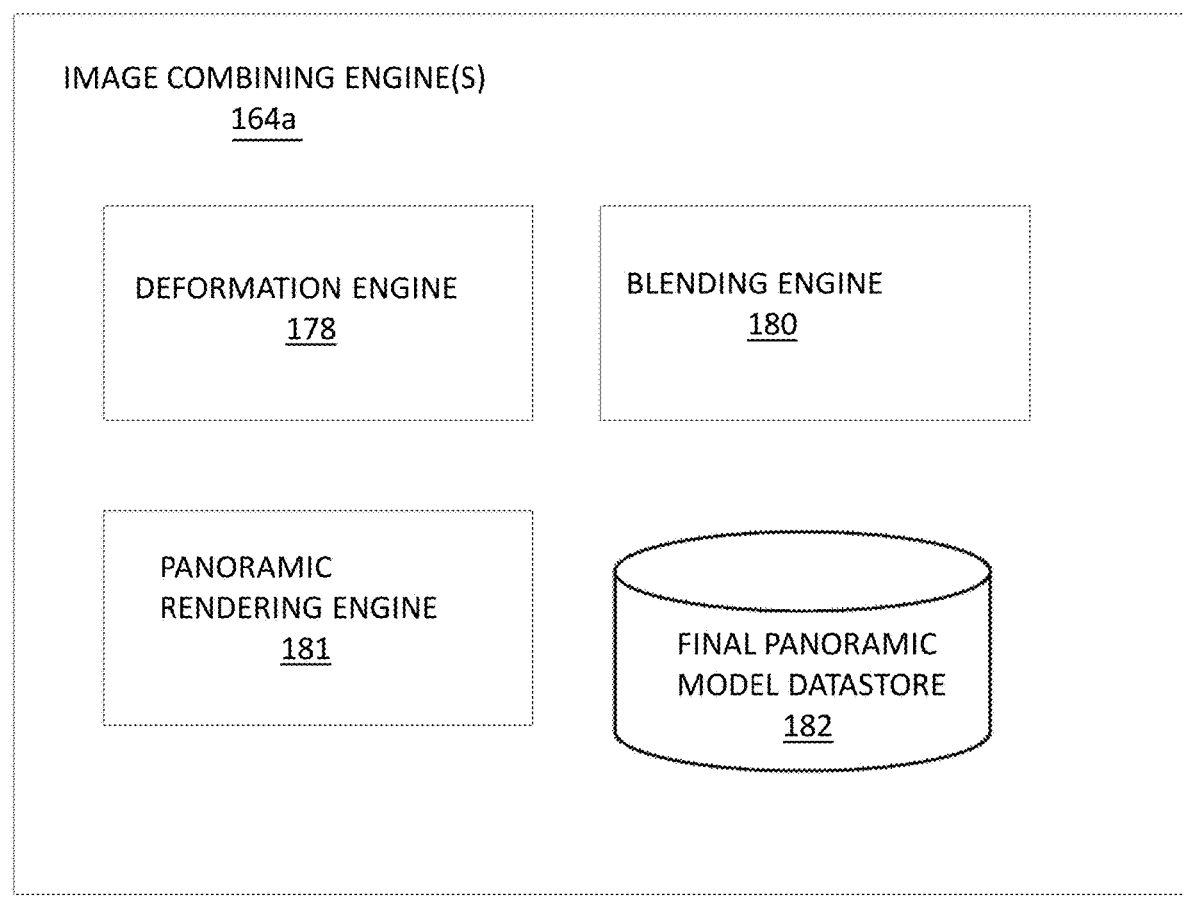
FIG. 1D is a diagram showing an example of an image combining engine(s).

FIG. 1D is a diagram showing an example of an image combining engine(s) 164a.

The image combining engine(s) 164a may include a deformation engine 178, a blending engine 180, a panoramic rendering engine 181, and a final panoramic model datastore 182. One or more of the modules of the image combining engine(s) 164a may be coupled to each other or to modules not shown.

The deformation engine 178 may implement one or more automated agents configured to register and/or deform the images in the initial panoramic model to match gradients at the boundaries of adjacent images. For example, some regions of the initial panoramic model may not register properly due to the various camera angles or perspectives used in building the model. In one implementation, the deformation engine 178 is configured to execute a global optimization method to identify the appropriate image deformation required to match the boundaries of adjacent images. Once the deformation has been identified, the deformation engine 178 can be configured to apply a deformation to the images of the initial panoramic model to deform the images.

The blending engine 180 may implement one or more automated agents configured to blend the images from the deformation engine to produce a final panoramic model for each key camera angle. In one implementation, the blending engine 180 can use Poisson blending for each key camera angle to use target gradients from non-blended images to produce a blended image with gradients that best match those target gradients. The final panoramic model can be rendered to the user as the average image with weights of barycentric coordinates of the triangles from the triangulated sphere that contains the key camera angle and the images (actual or approximate) corresponding to the vertices of the triangle.

The final panoramic model datastore 182 may be configured to store data related to the final panoramic model.

The panoramic rendering engine 181 may implement one or more automated agents configured to render the final panoramic model to the user for a chosen key camera angle.

Figure 2:
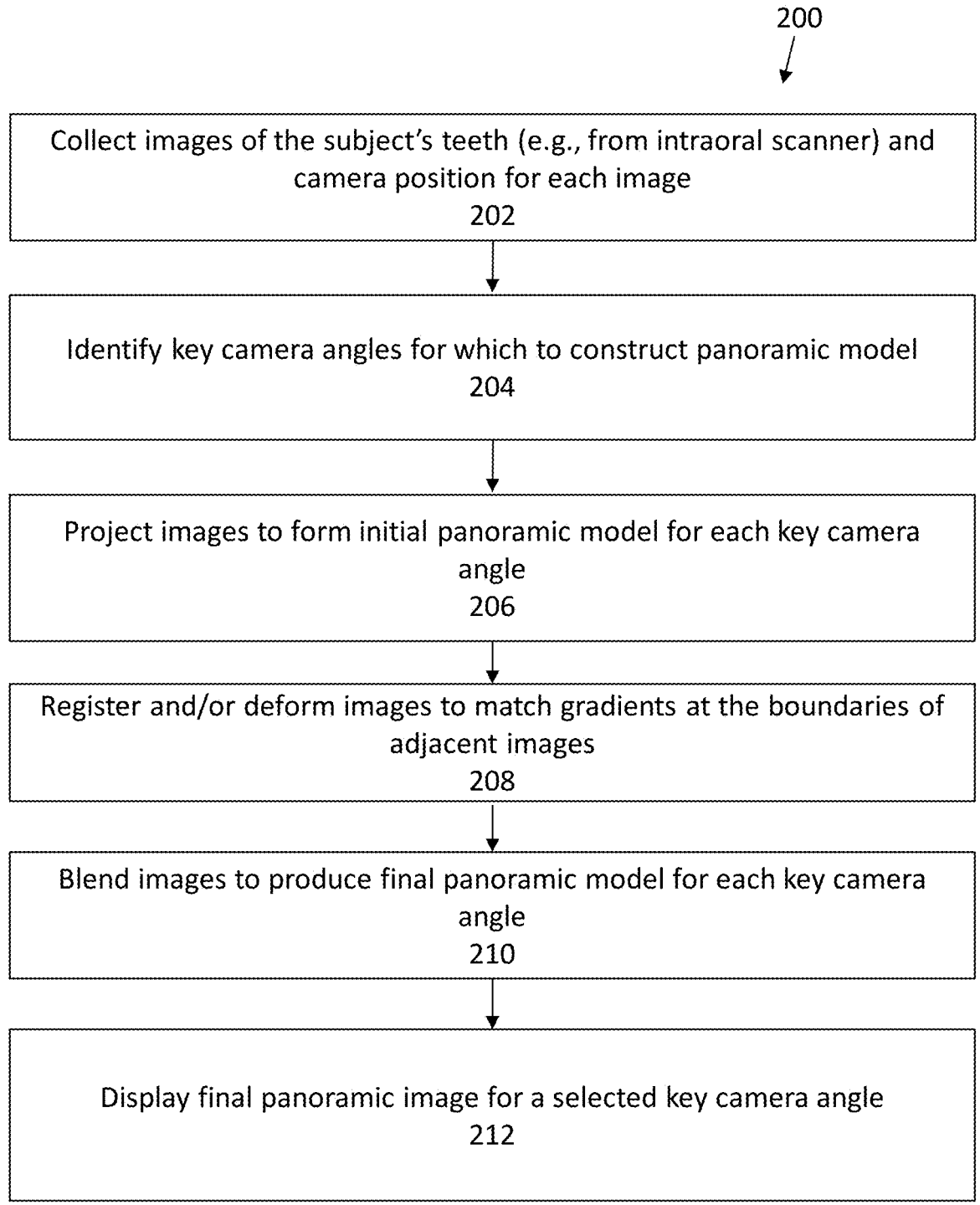
FIG. 2 is a flowchart describing an example of a process for generating a panoramic model of a subject's teeth from a plurality of images of the subject's teeth.

FIG. 2 illustrates a flowchart 200 that describes an imaging process for collecting, processing, and displaying a panoramic model of a subject's teeth. Referring to operation 202 of flowchart 200, the process includes performing a scan of a subject's intraoral cavity to collect images of the subject's teeth. This scan can be performed, for example, with an intraoral scanner or a camera system, as described above. In some aspects, the intraoral scanner or the camera system can record a plurality of discrete images or a series of continuous images (e.g., video) during the scan. Additionally, the precise position and orientation of the intraoral scanner or the camera system (for each image) can be tracked and recorded during the scan. The position and orientation of the intraoral scanner or camera system can further be associated with each respective discrete image or video frame. In another embodiment, a digital model of a patient's dental arch can be access or received (e.g., if the scan was previously performed).

Figure 3A:
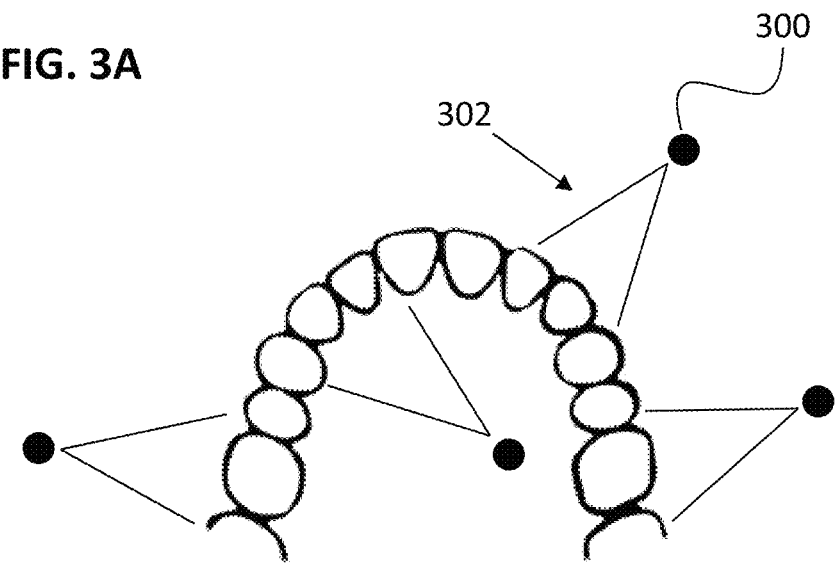
FIGS. 3A-3B illustrate performing a scan of a subject's teeth including acquiring images from a plurality of camera positions.
Figure 3B:
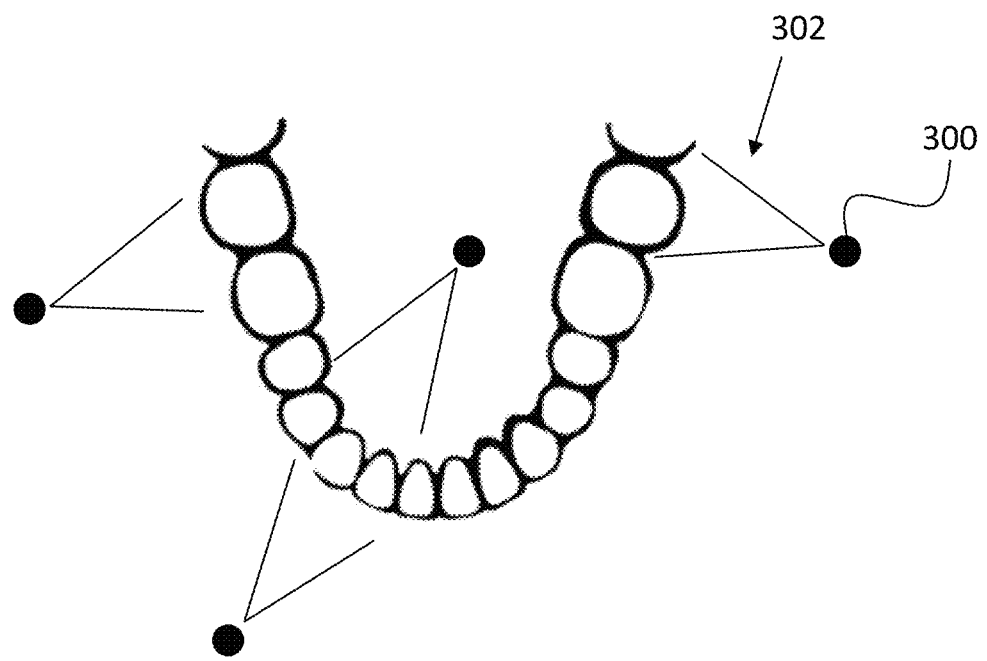
Figure 3C:
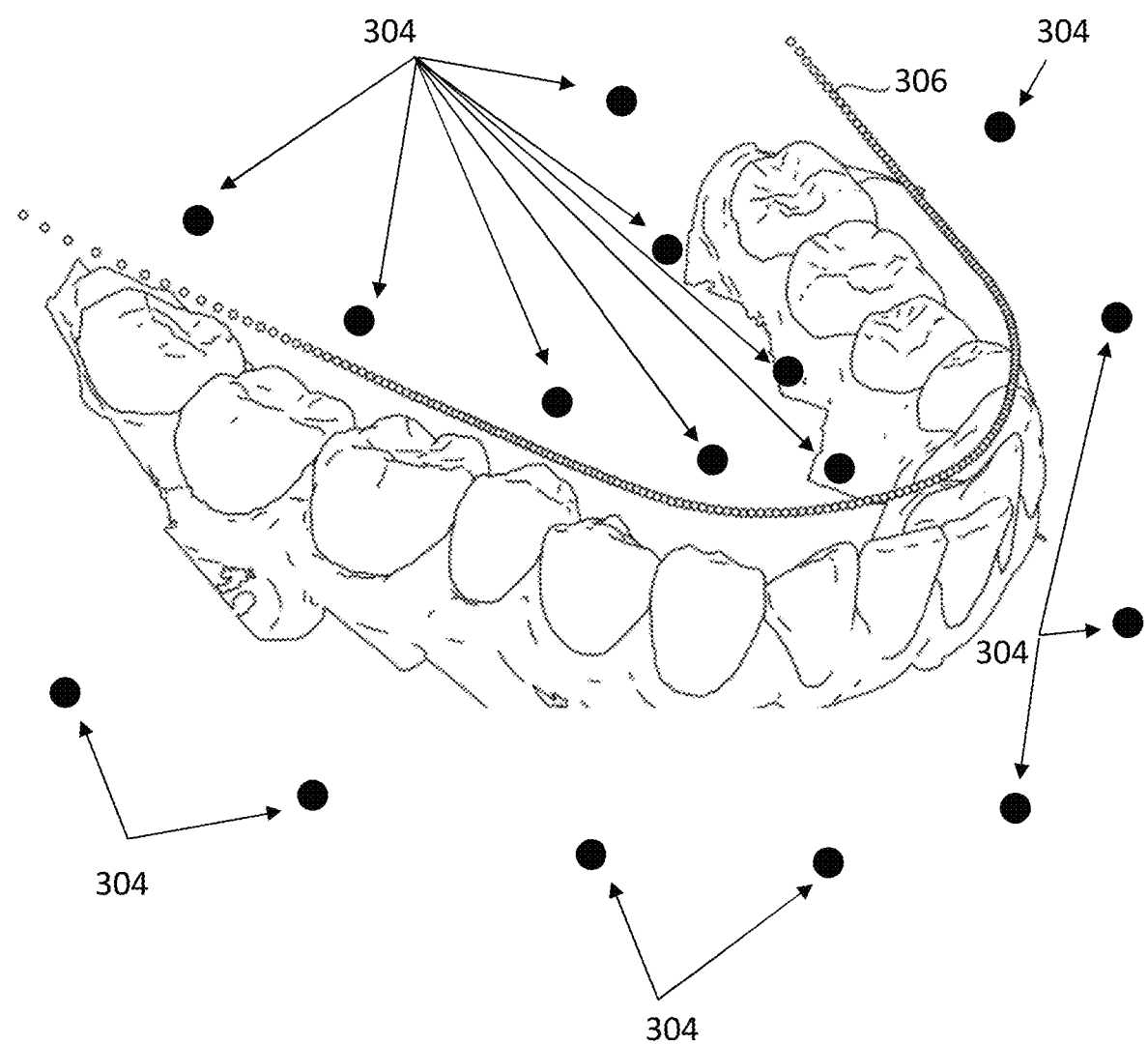
FIG. 3C illustrates generating a point cloud of all camera positions and images from the scan of the subject's teeth.

FIGS. 3A-3C represent a scan of a subject's intraoral cavity corresponding to operation 202 of flowchart 200, including the upper jaw (FIG. 3A) and the lower jaw (FIG. 3B). This scan can be performed, for example, with an intraoral scanner or a camera system, as described above. In some aspects, the intraoral scanner or the camera system can record a plurality of discrete images or a series of continuous images (e.g., video) during the scan. Points 300 represent the position and/or orientation of the intraoral scanner or camera system for each image that is acquired during the scan (i.e., the position and/or orientation of the approximate center of the aperture of the intraoral scanner or camera system). Field-of-view 302 represents the field-of-view for each image taken by the intraoral scanner or camera system. The intraoral scanner or camera system is scanned along all surfaces of both the upper and lower jaws to obtain images of all the relevant tooth surface structures.

Referring to FIG. 3C, a point cloud 304 of all camera positions and/or orientations can be recorded, including the images associated with each camera position and/or orientation of the point cloud. Additionally, the center jaw line 306 of the subject's intraoral cavity can be determined. In on example, the center jaw line can be determined by finding the maximal variance axis by applying a principal component analysis (PCA) on the camera positions from the point cloud 304. The other two axes of the center jaw line can be determined by applying quantile regression of a polynomial (e.g., of 4th degree) of each of the other two axes to the maximal variance axis. Thus, the center jaw line may be a center line of the received scan data, which (for intraoral scanner data) typically corresponds to the center jaw line.

Alternatively, the center jaw line may be solved or determined to correspond to the actual center jaw line from based on an analysis of the tooth images. Unless indicated otherwise, the center jaw line may refer to either the center line of the received data or an actual, estimated center jaw line.

Next, at an operation 204 of FIG. 2, the process includes identifying the key camera angles for which to construct a panoramic model. These key camera angles provide the view points for which panoramic models of the subject's teeth will be generated. Camera angles refer to the direction of view of the camera (i.e., the z-direction of the camera aperture) for the panoramic model.

Figure 4A:
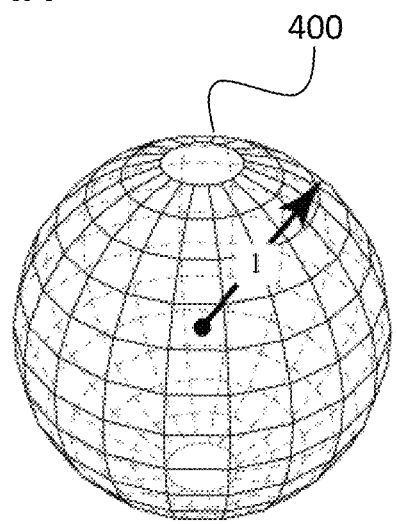
FIGS. 4A-4B illustrate generating a sphere and triangulating the sphere to identify the key camera angles required to build a panoramic model of the subject's teeth.
Figure 4B:
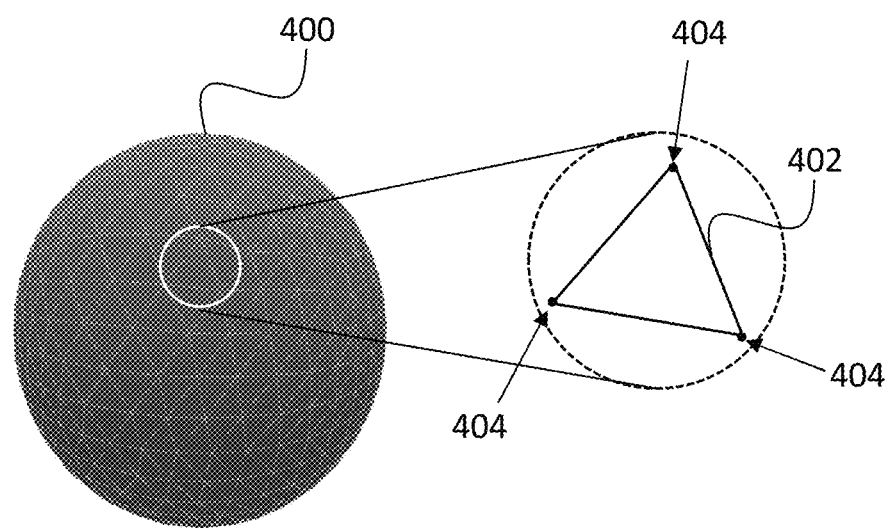

In one example, the camera angles for the panoramic model can be represented by a sphere, as illustrated by sphere 400 in FIG. 4A. All possible camera angles can be represented within sphere 400 as unit vectors originating at coordinate 0 (e.g., the center of the sphere). An example vector 1 is shown in FIG. 4A. Referring to FIG. 4B, the unit sphere 400 can be triangulated into a plurality of triangles 402 using any known triangulation method, such as, for example, by subdividing all triangles in an octahedron recursively. Vectors originating at coordinate 0 and ending at each vertex 404 of the plurality of triangles are identified as the key camera angles required for building the panoramic model.

Referring back to FIG. 2, at an operation 206, the process can include projecting images from the scan of the subject's teeth to form an initial panoramic model for each key camera angle. In one example, referring to FIG. 5, a two-dimensional grid can be formed by dividing the center jaw line 556 into equidistant segments 551 (represented by the points in FIG. 5), and forming a line 552 at each segment, the lines 552 being perpendicular to the center jaw line 556 and each key camera angle or direction 554 as selected in the prior step (e.g., the key camera angles that originate at coordinate 0 in the unit sphere 400 and end at each vertex 404 of the plurality of triangles in FIG. 4B). The end points of each line 552 can be indexed by the segment number and the line number to form the two-dimensional grid of points. Next, the point cloud of all camera positions during the scan is compared to the end points of each line 552, and the physical camera locations most suitable, for example the camera with orientation closest to the key camera angle for each of the points point are chosen. It should be noted that each of the lines 552 in FIG. 5, as indexed in the two-dimensional grid of points, may not have an exact match from the received scan data (e.g., the lines may be shorter than the distance between the physical camera position and the subject's teeth during the scan, or may otherwise not correspond to the exact position in space). In that case, the chosen images captured during that scan can be approximated with an orthographic camera to provide images from each of the end points. This results in a narrow field of view from the scan images being used to approximate the view from each of the end points. In some variations, as described in greater detail below, the approximated image may be a novel view corresponding to the grid of points (e.g., ends of the line or segments) that may be solved using an image-based rendering configured for use with the intraoral scanning data. The combination of all the approximated images at each of the end points in the two-dimensional grid of points results in an initial panoramic model of the subject's teeth for each key camera angle. FIG. 6A shows one example of an initial panoramic model 600 resulting from projection of multiple images.

As can be seen in FIG. 6A, some regions of the initial panoramic model 600 may not register properly due to the various camera angles or perspectives used in building the model. Thus, referring back to FIG. 2, at step 208 of the process, it may be necessary to register and/or deform the images in the initial panoramic model to match gradients at the boundaries of adjacent images. The deformation may include several distinct steps, such as a global optimization followed by a local optimization along the image boundaries only. In one example, a global optimization method (such as projective image alignment by using Enhanced Correlation Coefficient, or ECC, maximization) can be used to identify the appropriate image deformation required to match the boundaries of adjacent images. After applying the deformation identified in the global optimization, the image boundaries may still not match. Next a local optimization along the image boundaries only can be used to identify an appropriate deformation along the image boundaries required to match the boundaries of adjacent images. The identified boundary deformation can be analytically extended to the interior of each image to deform the images in a smooth and realistic manner.

Next, at an operation 210 of the process, the resulting images from the previous step can be blended to produce a final panoramic model for each key camera angle. In one example, Poisson blending can be used to produce the final panoramic model for each key camera angle, which takes target gradients from the non-blended images to produce an image with gradients that best match those target gradients. Each domain can be taken from a single image to preserve resolution.

Figure 6A:
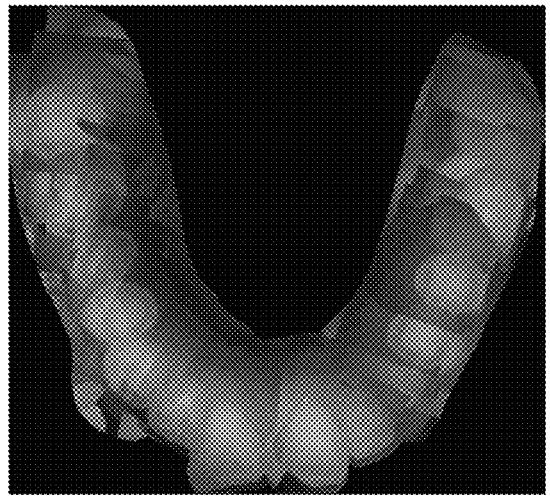
FIG. 6A is one example of an initial panoramic model before deforming and blending the images.
Figure 6B:
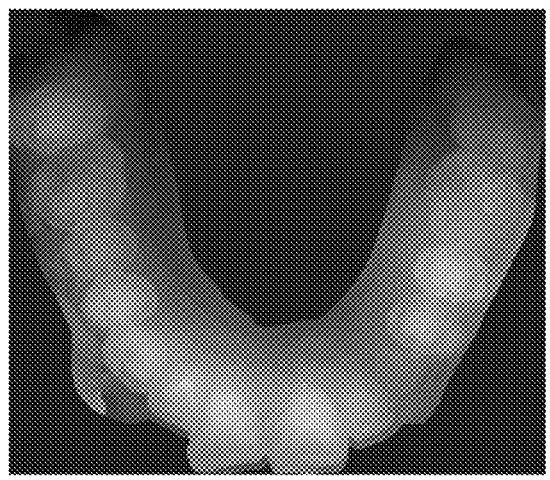
FIG. 6B is an example of a final panoramic model after deforming and blending the images.

Finally, at an operation 212 of the process, the final panoramic model can be displayed to a user for a selected key camera angle. The final panoramic model can be rendered to the user as the average image with weights of barycentric coordinates of the triangle described above (e.g., triangle 402 in FIG. 4B) that contains the key camera angle and the images (actual or approximate) corresponding to the vertices of the triangle. An example of a blended final panoramic model 602 from a key camera angle is shown in FIG. 6B.

Figure 7:
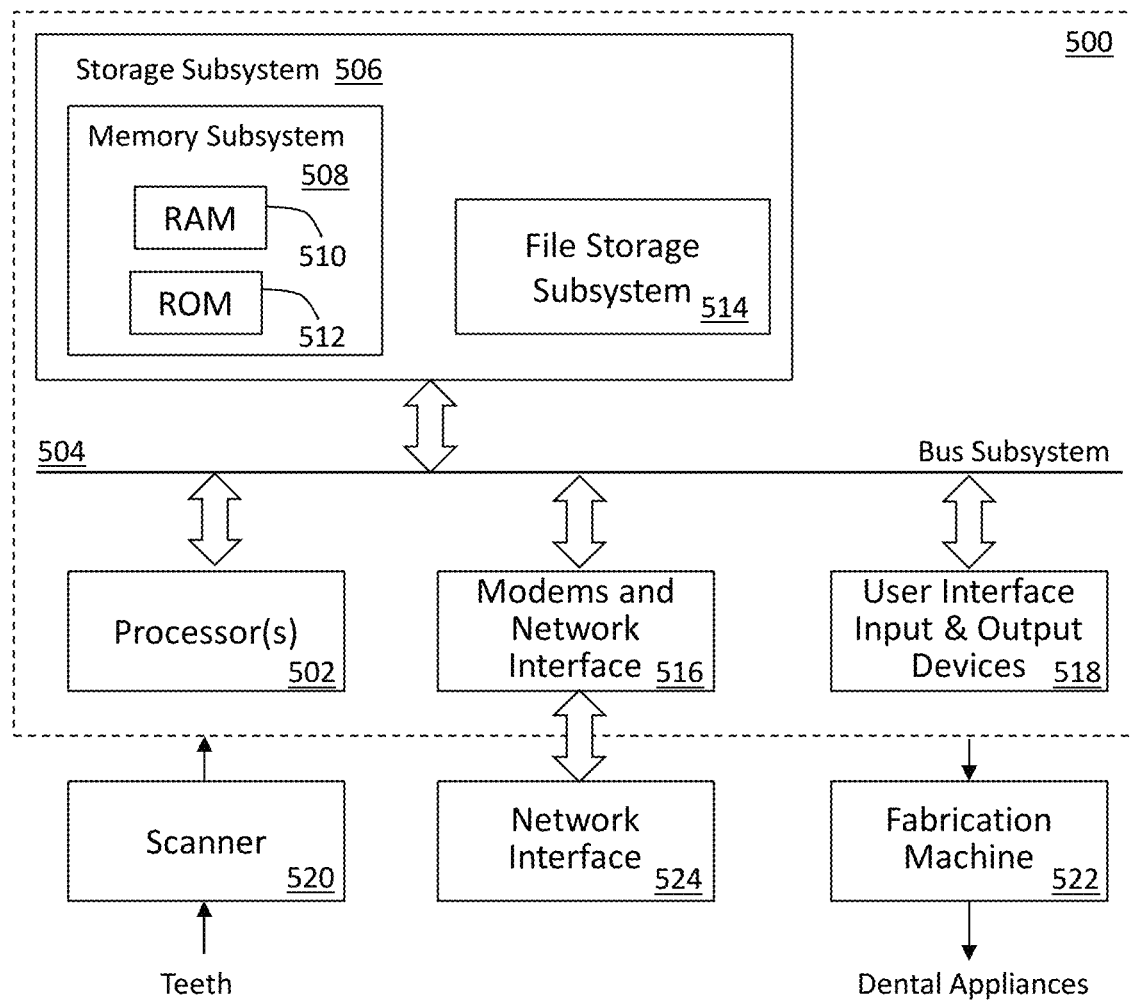
FIG. 7 is a simplified block diagram showing an example of a data processing system for designing and manufacturing an orthodontic aligner.

The methods described herein may be performed by an apparatus, such as a data processing system, which may include hardware, software, and/or firmware for performing many of these steps described above. For example, FIG. 7 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 808 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system). Distributed, such as cloud-based, instructions may also or alternatively be used.

File storage subsystem 514 provides persistent (nonvolatile) storage for program and data files, and may include, e.g., at least one hard disk drive and at least one floppy disk drive (with associated removable media) and/or flash memory. There may also be other devices such as a CD-ROM drive and optical drives (all with their associated removable media). Additionally, the system may include drives of the type with removable media cartridges. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but may include a number of buses such as a local bus and one or more expansion buses (e.g., ADB, SCSI, ISA, EISA, MCA, NuBus, or PCI), as well as serial and parallel ports. Network connections may be established through a device such as a network adapter on one of these expansion buses or a modem on a serial port. The client computer may be a desktop system or a portable system.

Scanner 520 (e.g., intraoral scanner) may be responsible for scanning the patient's teeth directly or scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

The dental appliance fabricated by the fabrication machine 522 can be designed to implement at least a portion of a treatment plan, comprising a shell having a plurality of cavities therein designed to receive teeth of a jaw.

The system 500 may include software and/or firmware for executing instructions on the processor(s) for performing any of the methods described herein. For example, the system 500 of FIG. 7 can include a non-transitory computing device readable medium having instructions stored thereon that are executable by a processor to cause a computing device to receive scan data (e.g., intraoral scanning data), via a computing device, and to generate and/or display novel views of the teeth from received data, to form one or more panoramic view or set of views (e.g., model) of the teeth from the received (including novel views) and/or displaying the one or more panoramic views of sets of views. In some variations the non-transitory computer device readable medium may include instructions for creating or modifying an orthodontic treatment plan, including a series of incremental tooth arrangements to define a proposed orthodontic treatment.

The methods and apparatuses described herein may be used to allow a user to select and view, including interactively viewing, virtually any image of the patient's teeth from intraoral scanned data. This may include visible light (including color) or any other frequency of light (e.g., florescent, infrared, e.g., near-IR, or the like); the scanned images input may include scans of different wavelengths. The same dataset may include multiple wavelengths (e.g., visible light/color, near-IR, florescent, etc.). For example, the dataset may include images taken from the same position with multiple wavelengths, or image taken at different positions with multiple wavelengths. Thus, the data received (scan data), e.g., scanned by an intraoral scanner, may be marked or otherwise identified (in some cases by the predetermined datafile structure, or by labels on the scanned images) indicating what the scanning wavelength is. This metadata may be included with other metadata (e.g. position, patient identifier data, date/time data, etc.).

These methods and apparatuses may be used with a user interface that allows the user to select the camera angle (e.g., key camera angle) to display from the patient's teeth. For example, a user interface may provide an image of the scanned teeth (e.g., a starting view), and a manipulation tool to allow the user to zoom in, zoom out, rotate, or simply select a position relative to the teeth to display. The user may also toggle between different wavelengths (visible light, infrared, florescent, etc.), or overlays of these. The displayed views may be panoramic views as described herein. In some variations the displayed views may be novel views derived from the scanned views as described herein. The methods and apparatuses may therefore allow the user to quickly and efficiently review scanned image data directly, without requiring the construction of a 3D model of the patient's teeth, as panoramic images. Although scanned data is typically taken close to the patient's teeth, gums and/or palate, so that individual images are limited in their field of view, the method and apparatuses for generating panoramic views as described herein allow extremely quick, continuous and accurate viewing of zoomed-out panoramic images, from virtually any arbitrary point around or outside of the oral cavity.

Figure 8:
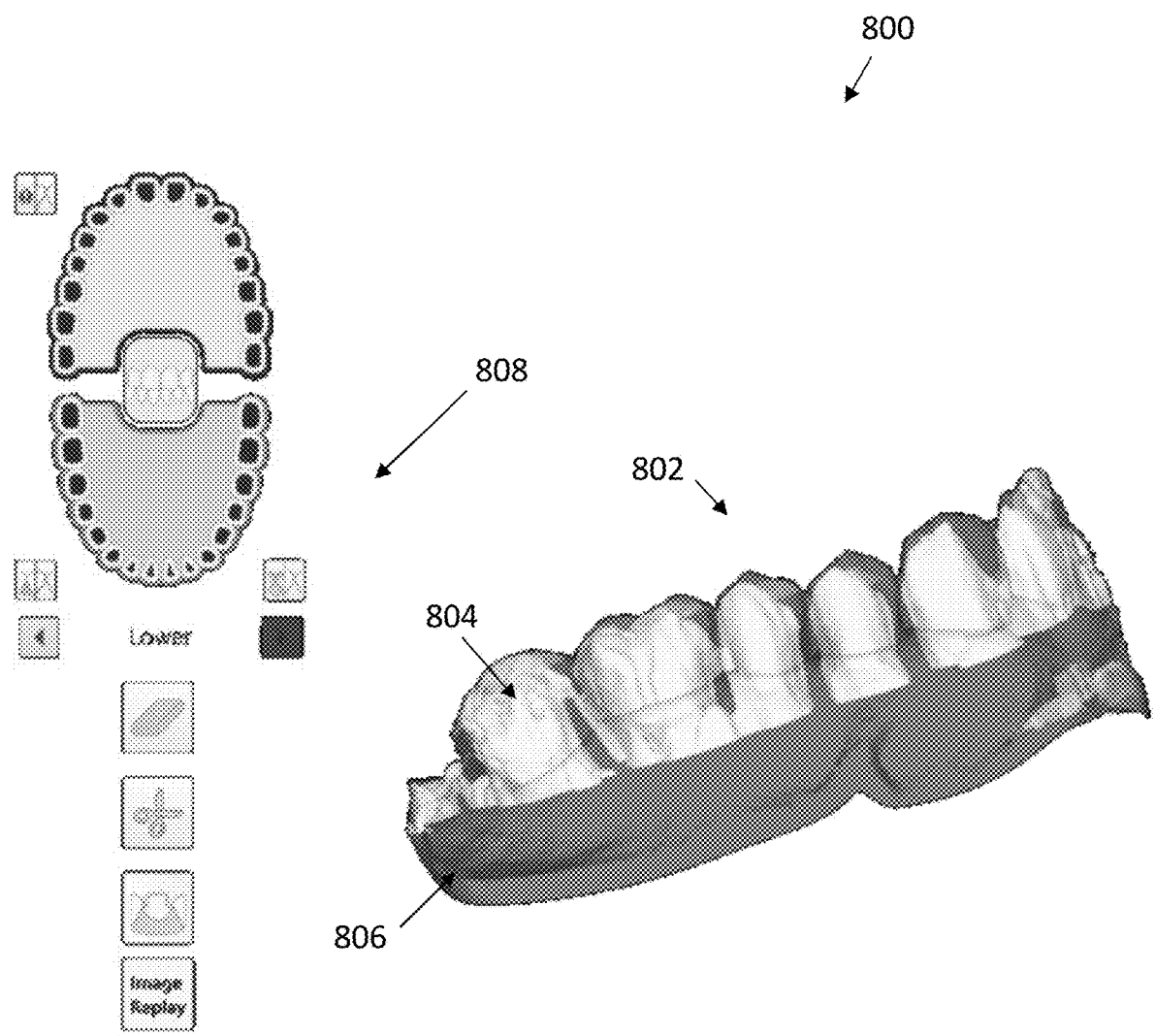
FIG. 8 illustrates an example user interface showing a 3D virtual model of a portion of a subject's teeth.

Thus, the devices and systems described herein can be configured to provide an alternative to volumetric visualization of a patient's dentition. For instance, internal structures of teeth can be seen using IR (e.g., near IR) light, which can be rendered in a 3D virtual model of the dentition. In some cases, external features of the teeth can also be rendered in the 3D virtual model by combining the scan data using the IR light with scan data collected using light sources emitting one or more other ranges of light wavelengths, such as visible light (e.g., fluorescent light). In some cases, the scan data includes X-ray data. FIG. 8 shows an example user interface 800 showing a 3D image of a lower jaw 802, which combines both near IR and visual light data. The internal structures 804 (e.g., collected using near IR) and surface features 806 (e.g., collected using visible light) may be rendered in different shades or colors on the user interface. The resolution of the 3D image may vary and, in some cases, be selected by the user. In some embodiments, the resolution for the internal structure is about 200 µm, thereby allowing the user to view the internal structure's morphology. Although this 3D image may be based on a reconstructed 3D model (derived from the scanned data) in some variations as described herein, this 3D model may be generated from panoramic data.

For example, a panoramic view may be equivalent to a view generated from a 3D reconstructed model, without requiring the use of a reconstructed 3D model. Because the displayed images may be taken directly from the scanned data (or from novel views derived from the scanned images, as described herein), there is little if any loss in the spectral information provided, which may necessarily occur when generating views from a synthesized 3D model. Thus, the reflection, transparency/translucence, hue, etc. information, including internal structures that may be difficult or impossible to reliably segment when forming a digital 3D model, may be preserved in the panoramic views, and/or panoramic models described herein.

In reference to FIG. 8, the image of the lower jaw 802 may instead be a panoramic view (panoramic, as it is formed of combined images from the intraoral scanner, as described herein) from an initial position, showing both visible light images 806 and near-IR images 804 (combined and/or overlapping). The view of the dental arch (e.g., lower arch) may be rotated, panned, zoomed, etc., by using one more user-interface input tools (e.g., buttons); movement is achieved visually by displaying different camera positions (angles) from the key camera angles for each panoramic view. The transition may be smoothly done to show continuous/smooth movement. The additional panoramic (e.g., wide-angle) views may be precalculated as part of a set (e.g., from a panoramic model) or may be calculated on the fly.

The user interface can allow the user to rotate the 3D model and/or zoom in on certain regions of the model. In some variations the user may zoom, pull/drag, and rotate the image of the teeth 802 using a mouse, touchscreen, etc. FIG. 8 illustrates example graphical user interface elements 808, which may also or alternatively allow the user to manipulate the 3D image in various ways, such as choose which portion of the dentition to show in the panoramic 3D view (e.g., upper jaw and/or lower jaw), remove or add layers (e.g., color, near-IR, florescent, etc.) and/or play/replay animations. In one implementation, the user interface allows the user to show and/or replay movement side-by-side of near IR and visual light images (and/or florescent images). In some embodiments, the user interface allows the user to select one or more regions of interest on the 3D image for zooming-in on. For example, the user may select a region using a magnifying loop or tool, to show a selected region of interest at higher magnification (e.g., again, generating a panoramic view of this subregion and/or identifying a particular specific view or generating a novel view from the scanned images corresponding to the zoomed-in camera angle). This may assist in diagnostics by improving diagnostic results confidence, and can help reveal defects, such as caries, within the teeth. A panoramic view of a penetrative wavelength (e.g., infrared, near-IR, etc.) can be used to visualize internal structures, without requiring a great deal of time and/or processor-intensive computation as compared to reconstructive techniques. The location of the caries as revealed by a panoramic view can be an indication as to the severity of the caries.

Figure 9:
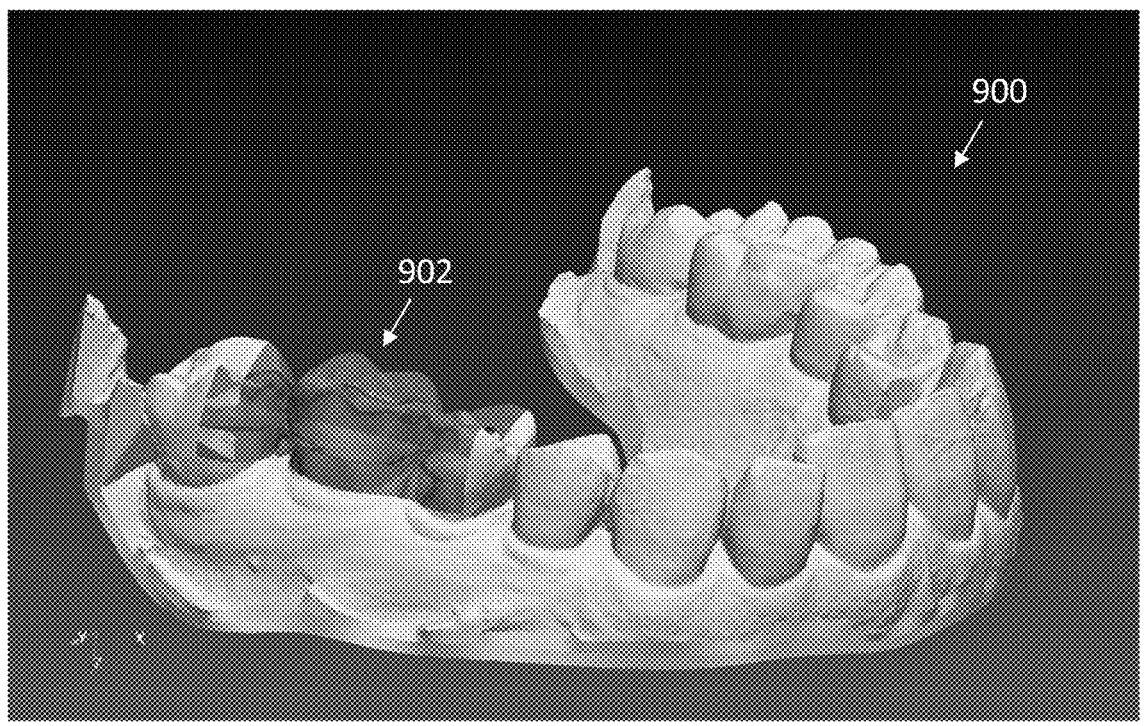
FIG. 9 illustrates an example 3D model of a subject's dental arch having partially transparent regions.

As mentioned, panoramic views of different wavelengths corresponding to the same viewing angles may be shown side-by-side or concurrently. For example, FIG. 9 shows another example 3D panoramic view 900 of a dental arch having a selected region 902. The selected region can correspond to a specified location of the teeth that may be shown using a different wavelength (e.g., IR, florescent, and/or visible light) images of the tooth/teeth than the rest of the view. In FIG. 9, a portion of the visible light panoramic view 901 in the selected region 902 is replaced with the corresponding portion of a near-IR panoramic view. This may allow the display of internal structures, e.g., as the partially transparent quality of IR (e.g., near-IR) images can allow the user to visualize a depth and volume of the internal structures. If both internal and surface structures are shown, the partially transparent region can allow the user to view internal and external features in relation to each other in a single model. The various internal and/or external features may be displayed with different shades and/or color based on certain aspects, such as density and/or composition.

In some embodiments, the user can choose which portion of the panoramic view to show as which wavelength(s). For example, the user may identify a certain portion of the 3D panoramic view as being a region of interest for further analysis. The user can then use the user interface to indicate this region to show either in greater detail and/or as near-IR where the near-IR data is included (e.g., in addition to the visible light and/or florescent images) from the scan data. Alternatively or additionally, the system may determine a suspected region of interest (e.g., based on density and/or composition) and display one or more panoramic views of the suspected region using the near-IR and/or florescent data. The user may zoom/pan/rotate the perspective (e.g., virtual camera) of the scanned data to access different viewpoints of the selected region 902. In some cases, the user can choose to render the entire dentition (or an entire dental arch) in near-IR, just visible light and/or just florescent.

Figure 10:
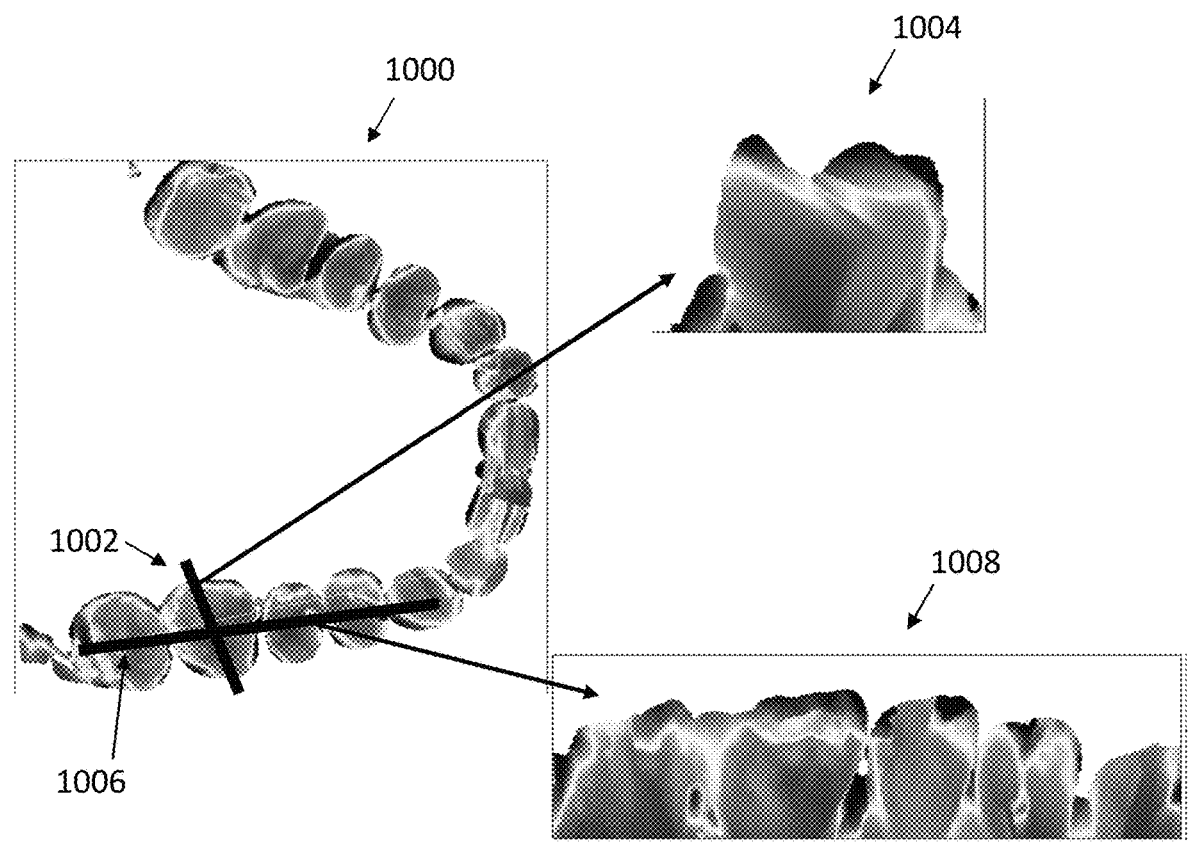
FIG. 10 illustrates an example dental arch rendered in various slice views.

In some embodiments, at least a portion of the dentition can be viewed in a slice presentation. FIG. 10 shows an example virtual sectioned model 1000 of a dental arch and slice views 1004 and 1006 generated from a panoramic model. The slice views can generated based on a virtual plane that is passed through at least a portion of the panoramic view. A section through the view may be calculated from the scan data and the panoramic image(s). The resulting section may be shown in a panoramic view. The location of the virtual plane (e.g., height and angle) can be determined with respect to a reference. In some embodiments, the reference may correspond to a reference plane or line (e.g., center jaw line or a gum line). In one implementation, the user may position and/or draw a first line 1002 across a selected tooth to pass a first virtual plane through a tooth, to generate a corresponding first slice view 1004 of the tooth. Likewise, a user may position and/or draw a second line 1006 across a selected region of dental arch to pass a second virtual plane through the selected region of the arch, to generate a corresponding second slice view 1008 of the region. The slice views may be generated using data obtained using one or more modalities (e.g., IR and/or visible light) of the scan(s). Thus, the slice views can reveal corresponding internal and/or surface structures of the teeth. In some embodiments, the slice views may be generated using data collected using only one modality (e.g., IR or visible light), for example, to save computational time. The slice views may correspond to 2D images, or may correspond to sections having a specified thickness generated from the original data and/or panoramic views. In the slice views, various features may be represented in different shades and/or colors to represent, for example, different densities, composition (e.g., teeth, caries, gingiva) and/or other aspects of the dentition. In some embodiments, density calculations and/or other data associated with the slice views can also be displayed to the user. In particular, the slices described herein may be derived from a panoramic view.

Figure 11:
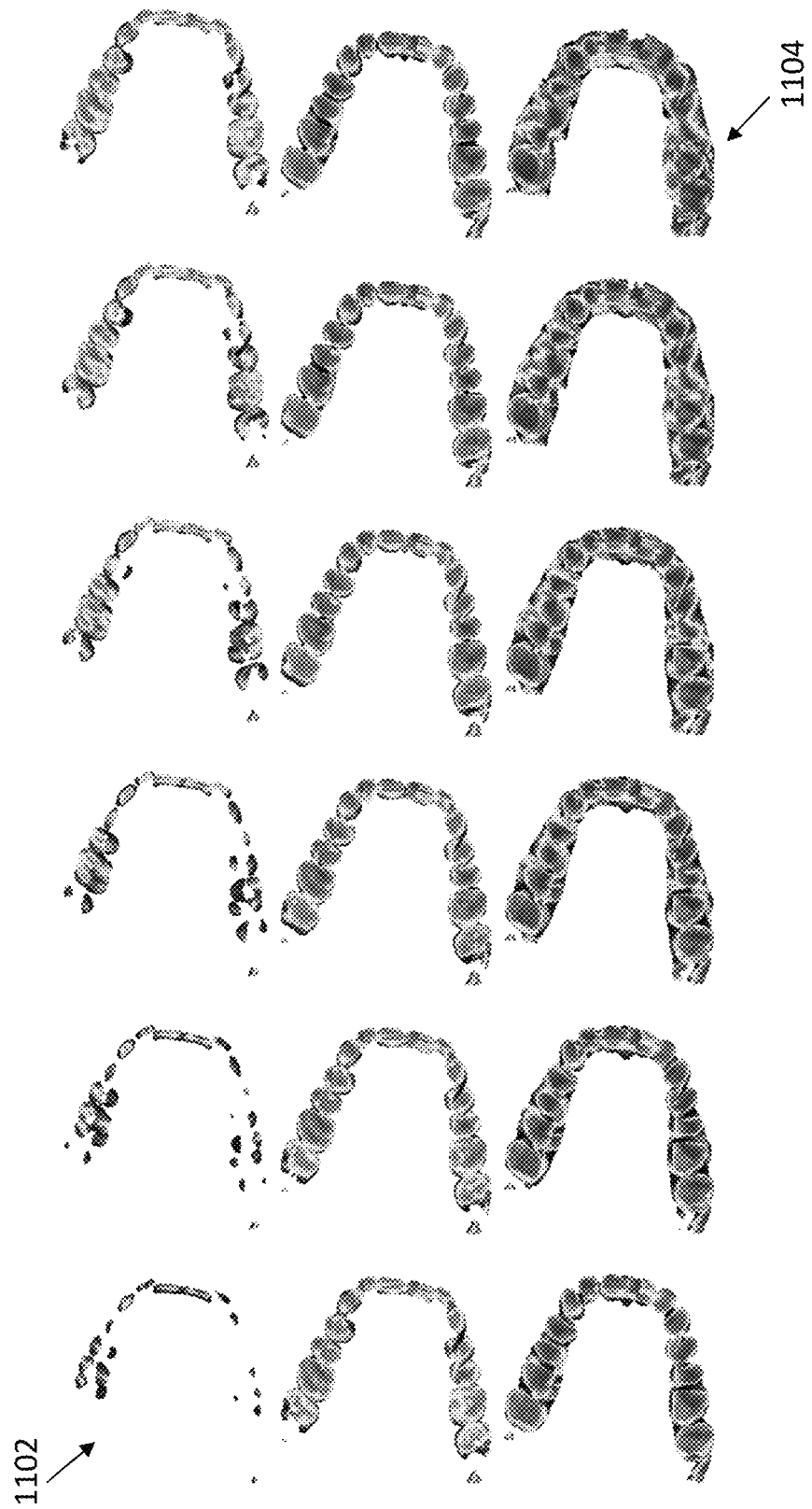
FIG. 11 illustrates another example of a dental arch rendered in slice views along horizontal cuts.

FIG. 11 shows another example showing slice views from a series of cuts though a dental arch. In this example, the series of slice views represent a progression of horizontal cuts through the arch, from a first slice 1102 through a lower portion of the dental arch nearest to the gum line to a last slice 1104 representing an upper portion of the dental arch including the occlusal surface of the teeth. The slice views may include different shadings and/or colors to indicate different density, composition and/or other aspects of the dental arch. This representation can allow the user to analyze different aspects of the teeth in relation to the roots, gum line and/or occlusal surfaces. For example, the depth and height of dental defects, such as caries, may be easily observed. The user interface may allow the user to choose the number of slices through the dentition. The user interface may allow the user to manipulate each of the slice views, for example, by moving, overlaying and/or rotating the slice views. In some embodiments, the user interface allows the user to animate the slice views. For example, the user interface may display slices 1102 to 1104 in a series of images showing the progression moving from the lower portion to the upper portion of the dental arch, or vice versa.

The panoramic views described herein can be render the subject's dentition in any of a number of ways. In some embodiments, the panoramic views simulate a bitewing view of the dental arch. Traditionally, a bitewing is an X-ray film of the crowns of upper and lower teeth which are taken simultaneously with a tab or paper held in place between the teeth. Bitewing views typically show at least a portion of the dental arch, and can include the crowns of the teeth to about the level of the supporting bone. In practice, bitewing views are often used to detect evidence of any cavities between the teeth, diagnose an abscess or a cyst, and to show any changes to the roots of the teeth and surrounding bone. The panoramic viewing techniques can be used to generate simulated bitewing views of a dental arch so that a dental practitioner can view aspects of the patient's dentition similar to a traditional X-ray bitewing image.

Figure 12:
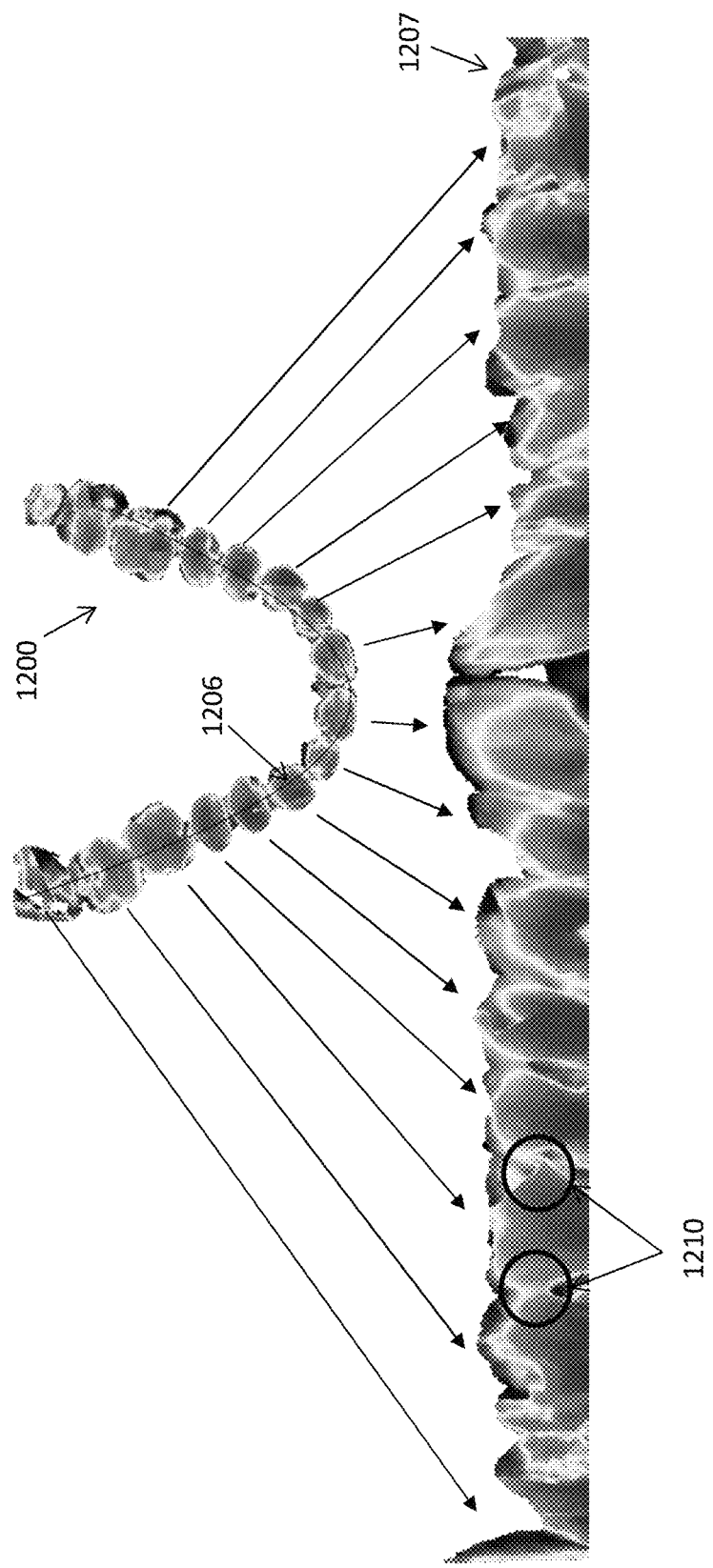
FIG. 12 illustrates and example how scan data of a curved dental arch can be used to generate a panoramic view where the teeth are aligned in a row.

In some cases, the simulated bitewing view depicts the teeth within a dental arch along a straight line rather than along the curvature of the jaw center line. FIG. 12 demonstrates how scan data of a curved dental arch 1200 can be used to generate a bitewing view 1207 with teeth aligned in a row, in accordance with some embodiments. As shown, the jaw center line 1206 of the curved dental arch can be straightened to effectively "unwind" the dental arch. Thus, in the example shown, the bitewing view depicts the teeth along a row. The bitewing view shows the teeth of the dental arch from the perspective of a particular viewing angle. In the example of FIG. 12, the teeth are viewed from a buccal viewing angle such that regions of interest 1210 in inter dental regions can be viewed from a buccal perspective. The regions of interest 1210 may be identified, labeled and/or analyzed for defects. Other viewing angles may include occlusal or lingual viewing angles. The particular viewing angle can be selected by a user and/or automatically selected (e.g., default setting). As will be described herein, in some variations, the panoramic view may concurrently show buccal, lingual and occlusal surfaces (as will be descried in reference to FIGS. 17A-17C and 18A-18B.

A center jaw line 1206 can be identified using the collected the scan data and can be determined using any of a number of techniques. Since center jaw line is used as a reference, in some cases, the center jaw line may be approximate and does not need to be exactly at the center of the jaw at every point along the jaw. In some embodiments, the center jaw line is approximated based on the images of the teeth and/or 3D scan data of the teeth. In some embodiments, the center jaw line may be determined by finding the maximal variance axis (e.g., by applying a principal component analysis (PCA) on the camera positions from a point cloud), as described. In some cases, the center jaw line is determined using only the collected position of the camera during the scan. For example, if the scan involves moving the scanner around the dental arch (e.g., from buccal, occlusal and lingual sides), the center jaw line may be approximated as an arched curve along the center of the scanning path. In some cases, the user may manually enter and/or change the center jaw line or portions of the center jaw line.

Figure 5:
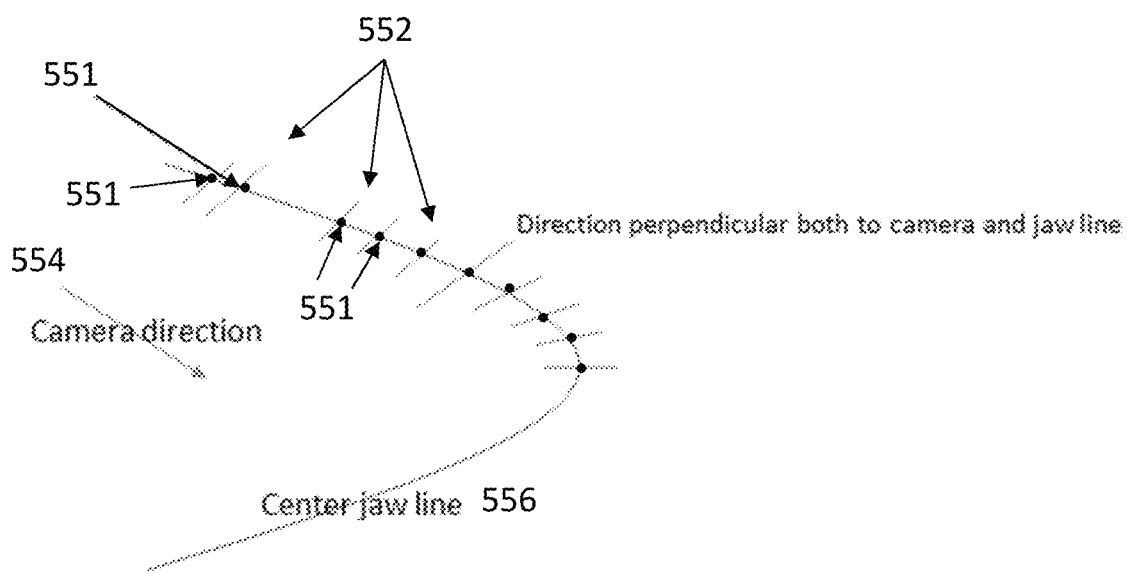
FIG. 5 illustrates one technique for generating a two-dimensional grid of points required for generating a panoramic model of the subject's teeth.

Once the center jaw line is identified, virtual pixels for constructing the panoramic view can be marked along the center jaw line for constructing the panoramic view (similar to the points/segments along the center jaw line of FIG. 5). In some embodiments, the virtual pixels are equidistantly distributed along the center jaw line. The virtual pixels may be spaced apart by a predetermined distance, for example, for generating an image having at least or at most a certain resolution. In one implementation, the resolution is about 200 μm. To select the appropriate images for generating the panoramic view at the particular viewing angle, a virtual camera can be passed along a path in accordance with the center jaw line such that the virtual camera direction is at the particular viewing angle with respect to the center jaw line. For example, in one implementation for generating an occlusal panoramic view, the jaw center line is along the xy plane and the virtual camera direction is in the z direction with respect to the center jaw line. For each pixel, the image(s) that has/have an associated viewing angle is/are most closely aligned with the particular viewing angle is identified and projected on a virtual screen that is perpendicular to the virtual camera direction. For instance, for an occlusal panoramic view, the image(s) that is/are most closely aligned with an occlusal viewing angle (e.g., 90 degrees) is/are identified and projected onto a corresponding virtual screen. This process is continued as the virtual camera travels with respect to the center jaw line for each pixel until all the pixels have associated images projected onto corresponding virtual screens to generate a panoramic view of the dental arch. In this way, each pixel can be associated with one or more images, which can collectively be used to generate a panoramic view of the dental arch from a selected viewing angle. That is, the selected images for each of the virtual pixels can be projected onto corresponding virtual screens and joined together to construct the panoramic view. In some instances, only one image is selected per pixel. In other instances, more than one image (e.g., 2, 3, 4, 6, etc.) are selected per pixel. In some cases, all of the teeth in the dental arch are shown in the panoramic view (e.g., so that the dental practitioner may view all the teeth in one image). In other cases, only a portion of the teeth in the dental arch are shown in the panoramic view (e.g., if the dental practitioner wants to view only a portion of the dental arch).

As described herein, the center jaw line can be "unwrapped" so that the teeth are presented in a row (straightened center jaw line). One of the advantageous of depicting the dental arch along a single row is that the dental arch can be displayed as a narrow elongated image, thereby taking up less display real estate and being conducive to stacking and comparing with other panoramic views. However, the panoramic views may render the dental arch in any of a number of ways. The identified images can be projected on to a virtual screen for each pixel independent of the curvature of the center jaw line. Thus, the collection of identified images in the panoramic view can be rendered along a line having any shape. In other embodiments, the dental arch is presented in accordance with a curved center jaw line, such as the natural curve of the actual dental arch, or in a different curvature that is conducive to viewing an analyzing certain aspects of the teeth. In some embodiments, the view includes an occlusal view showing the different quadrants of a dental arch.

The images selected to generate the views (and any of the panoramic views described herein) can include those collected using any type of scanning modality (e.g., IR, visible light, florescent, X-ray, etc.) or combination of scanning modalities. The example of FIG. 12, the panoramic view is generated from near IR images, which show internal structures of the teeth. In other examples, the panoramic view can be generated from images collected using different scanning wavelengths of light. For example, a panoramic view can be generated using images collected using visible light (e.g., fluorescent light) or X-ray. In some implementations, images collected using two or more modalities can be the combined to generate images that depict different aspects of the dentition (e.g., internal and surface features of the teeth). In other implementations, the images collected using only one modality is used to generate the panoramic view(s), which may allow the images to be processed and displayed more quickly, and expend less computational power.

Figure 13A:
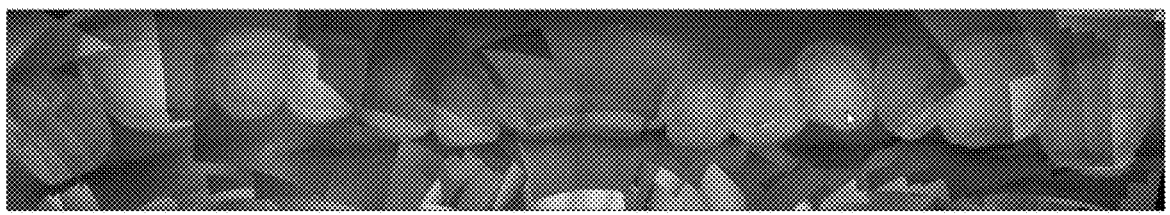
FIGS. 13A-13C illustrate examples panoramic views of a dental arch before and after a blending operation and at different viewing angles.
Figure 13B:
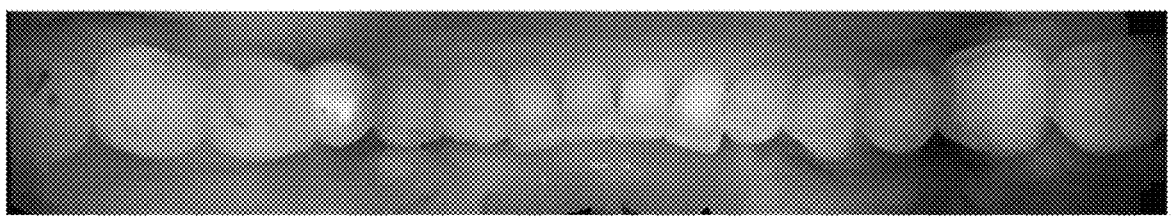

FIGS. 13A and 13B show examples of panoramic views (e.g., bitewing views in these examples) of a dental arch at an occlusal viewing angle. FIG. 13A shows a raw panoramic view of stitched-together images prior to implementing a blending operation. As shown, the various selected images may overlap and have different shadings, colors and/or deformations related to the condition in which each image was taken. FIG. 13B shows the panoramic occlusal view of FIG. 13A after implementation of a blending operation to register and/or deform corresponding raw panoramic views to match gradients at the boundaries of adjacent images. As described herein, a deformation may include a global optimization and/or a local optimization along the image boundaries. In one example, a global optimization method can be used to identify the appropriate image deformation required to match the boundaries of adjacent images. If the image boundaries still do not sufficiently match after the global optimization, a local optimization along the image boundaries (e.g., only along the image boundaries) can be used to identify an appropriate deformation along the image boundaries required to match the boundaries of adjacent images. The boundary deformation may be extended to the interior portion of each image to deform the images in a smooth and realistic manner.

Figure 13C:
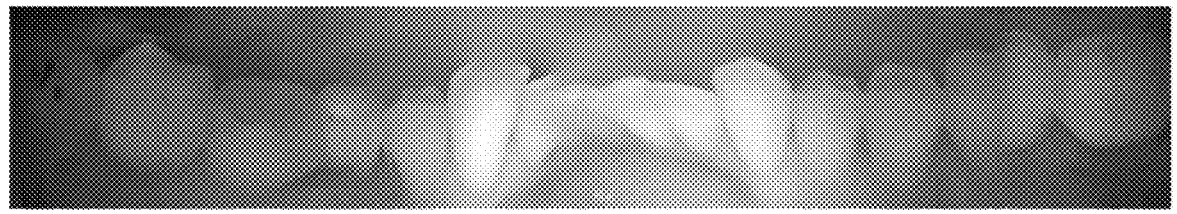

FIG. 13C shows a panoramic lingual view of the dental arch of FIGS. 13A and 13B and after a blending operation. Thus, various views of a dental arch can be generated based on a chosen viewing angle. In some embodiments, the system is configured to allow the user to choose the viewing angle, and the system will automatically update the panoramic image on the computer display based on the user's input. In some cases, the panoramic image can be updated in real time or near real time. In some cases, the panoramic image can be updated in about 15 seconds or less. The user interface for allowing the user to choose a viewing angle may vary. In some cases, the user can select the panoramic image with the cursor and rotate the image (e.g., up or down on the computer display) to select among various viewing angles. The panoramic image may quickly update to provide smooth transitions between the various viewing angles. In some embodiments, the user interface include one or more buttons, scroll bars, and/or other functional features for selecting viewing angles.

In either bitewing or non-bitewing (e.g., pseudorealistic, realistic, such as that shown in FIGS. 6A-6B) panoramic views, the simulated panoramic views (and any of the panoramic views described herein) can be generated from images generated by one or more machine learning agents. Such synthesized images may be generated based on real images taken during one or more scans or based on synthesized novel views generated from the scan data where the scan data does not include a scan taken at a specified position. In some variations a novel view may be generated using image-based rendering machine learning agent, as described herein. For example, a machine learning agent (e.g., a machine learning algorithm) can be configured to identify patterns in the real images, then use the identified patterns to create the novel ("synthetic") images. Synthesized images may be useful, for example, if there are not enough images to select from at a particular position and viewing angle to generate a panoramic image with sufficient detail or resolution. For instance, if the camera was not in an exact angle to show a particular image of one or more teeth, the system can generate such an image and use the synthesized image to render a more detailed panoramic view. In one example, a first and consecutive second scanned image may be collected during a dental scan from a particular viewing angle. However, there may not be enough data collected to provide images between the first and second images to generate a sufficiently detailed panoramic image. A machine learning algorithm can generate one or more novel, synthesized, images at the particular viewing angle corresponding to one or more real images between the first and second imaged. The synthesized image(s) can then be used along with the first and second images (and any other selected or synthesized images) to generate the panoramic view. In other examples, the machine learning algorithm may use data collected from one or more viewing angles different than a specified viewing angle to generate a synthesized one or more images at the specified viewing angle. A panoramic view can be generated solely based on synthesized images.

Figure 14A:
FIGS. 14A-14C illustrate examples panoramic views of another dental arch taken using different scanning modalities and at different viewing angles.
Figure 14B:
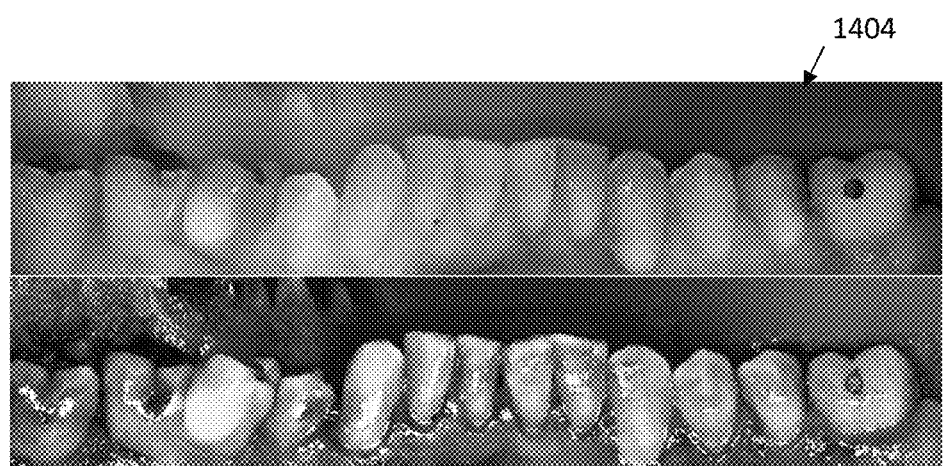
Figure 14C:
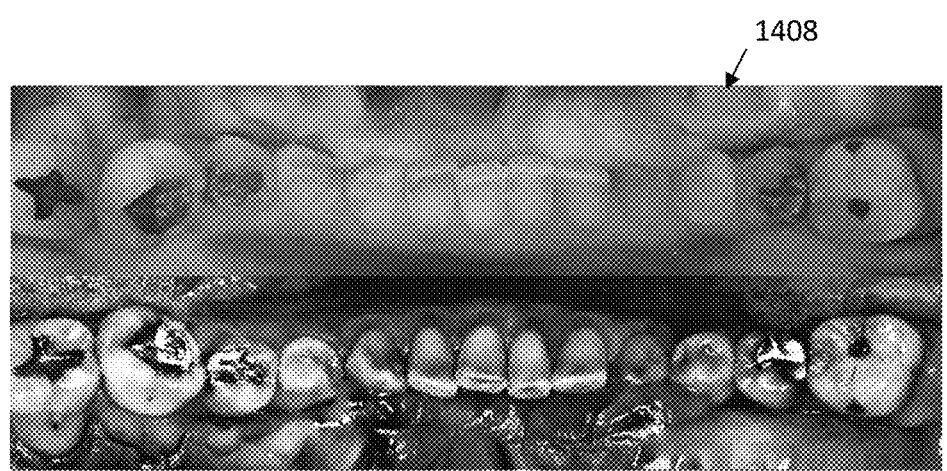

FIGS. 14A-14C show panoramic views of another dental arch at various viewing angles taken using different scanning modalities. FIG. 14A shows two lingual views of the dental arch, including a panoramic view 1400 using images taken with near-IR light and a panoramic view 1402 using images taken with visible light. FIG. 14B shows two buccal panoramic views of the dental arch, including a near-IR view 1404 and a visible light view 1406. FIG. 14C shows two occlusal panoramic views of the dental arch, including a near-IR view 1408 and a visible light view 1410. Displaying panoramic views using different modalities can allow the user to visualize different aspects of the patient's dentition. For example, some tooth features and defects (e.g., surface features) may be more easily identified using visible light and other tooth features and defects (e.g., internal structures) may be more easily identified using near-infrared light. These examples also illustrate how the various panoramic views can be stacked and aligned for easy comparison (particularly as compared to realistic/pseudorealistic views).

Note that the bitewing panoramic views presented in FIGS. 12, 13A-13C and 14A-14C are presented as examples only, and other viewing angles and scanning modalities may alternatively or additionally be presented on a computer interface. For example, panoramic views of a dental arch at angles between the lingual view and the occlusal view and/or between the occlusal view and the buccal view may alternatively or additionally be generated and displayed. Such views may be generated using real images collected during the scanning operation(s) and/or be generated using synthesized images created via machine learning. Additionally or alternatively, images taken using other scanning modalities, such as those using specific ranges of electromagnetic radiation (e.g., UV light, IR light, fluorescent light, X-ray, etc.), may be taken by the scanner to generate corresponding panoramic images. As described above, the panoramic views, including the bitewing panoramic views, may be rotated, zoomed, panned, etc. using a user interface. The rotation/zoom/pan of the bitewing panoramic view may be done smoothly in a continuous manner, including allowing the user to manipulate the user interface to move (pan/zoom/rotate) the view. The bitewing and non-bitewing panoramic views may be concurrently displayed.

A user interface can arrange various panoramic views, including but not limited to bitewing panoramic views, in any of a number of ways. For example, any of the panoramic views may be vertically aligned (e.g., stacked) so that features within the images are vertically aligned. In some cases, various panoramic views are horizontally arranged (side-by-side). Alternatively or additionally, the panoramic views may be overlappable and/or displayed as partially transparent so that features can be aligned and presented on top of each other. The user interface may be configured to allow the user to move one or more of the panoramic images, for example, using a drag and drop feature. In some cases, the user interface may allow the user to mark/label a region of interest in one or more panoramic views. In one implementation, the user can label a region of interest in one panoramic view, and the system generates a corresponding label at the corresponding location in another panoramic view. The user interface may be configured to present a single panoramic view that is switchable to other panoramic views at different viewing angles and/or scanning different modalities. In some embodiments, the user may scroll or rotate a panoramic view (or a user interface button) to display the various viewing angles and/or scanning modalities. For example, the user may view the dental arch in a lingual view, rotate the image to render an occlusal view, and rotate further to render a buccal view. In another example, the user may view the dental arch taken in an IR light modality and rotate the image to render the dental arch taken in a visible light modality. The system can be configured to continuously update the views as the user rotates the images. In some cases, the images may be rotated in both directions.

Any of the panoramic views may be presented in color and/or greyscale on the computer screen. In some instances, the user interface allows the user to choose whether to display the panoramic view(s) in color or in grey scale. The user interface may be configured to present features in two or more different colors (e.g., 2, 3, 4, 5, etc.). The different shades and/or colors may be used to visualize different aspects of the dentition. For example, the gingiva may be displayed in one shade and/or color, while teeth may be displayed in another shade and/or color. In some embodiments, regions with the teeth having different densities, compositions or other attributes are rendered with different shades and/or colors. For example, regions of the teeth having normal tooth composition be displayed in one shade and/or color, while regions of teeth having defective tooth composition (e.g., caries) may be displayed in another shade and/or color.

The user interface may be configured to present the panoramic views based on the time in which a scan was taken. In one instance, a first scan is taken of the patient's dentition at a first time (e.g., before an orthodontic treatment) and a second scan is taken of the patient's dentition at a second time (e.g., after an orthodontic treatment, or after a portion of an orthodontic treatment). The system can be configured to generate and display a first panoramic view based on the first scan and a second panoramic view based on the second scan. Likewise, the system may be configured to generate multiple (e.g., 2, 3, 4, 5, 6, etc.) panoramic views based on scan time. In this way, the user can easily visualize changes to the dentition over a period of time, for example, before and after treatment. In some instances, the user interface is configured to display such time-based images in a time-lapse presentation, where the progression of changes to the dentition are displayed in sequence to the user. For example, a first panoramic image can morph into a second panoramic image, which can morph into a third panoramic image, etc. In some cases, the morphing appears as an animation. The user may be able to change the speed in which the time-lapse images are displayed. Additionally or alternatively, the user may be able to stop the time-lapse presentation at any point, for example, to examine a particular image.

Figure 15:
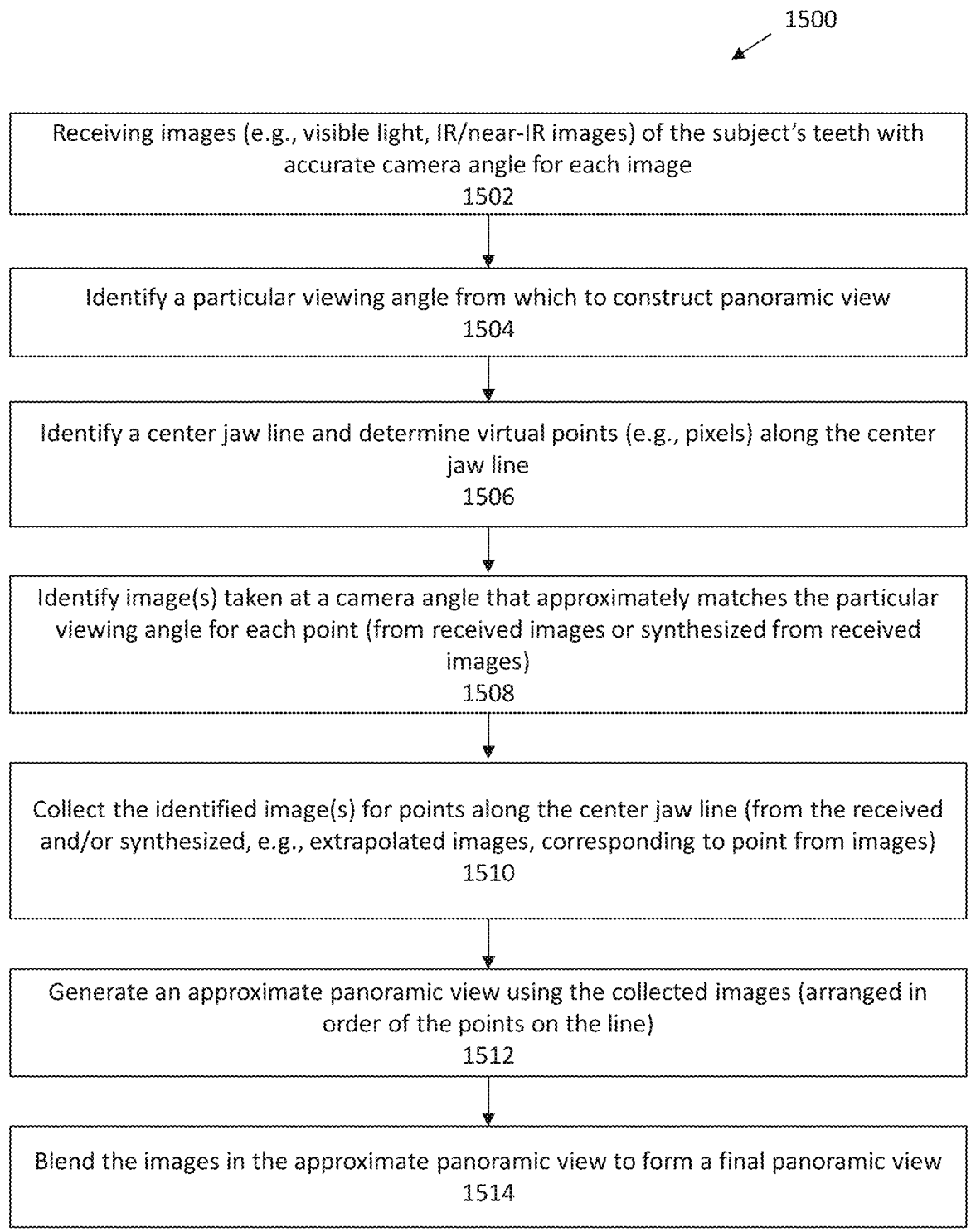
FIG. 15 is a flowchart describing an example of a process for generating a panoramic view (e.g., a bitewing panoramic view) of a subject's dentition.

FIG. 15 illustrates a flowchart 1500 that describes a process for generating a panoramic view of a subject's teeth. Referring to operation 1502, the process may include receiving images of the subject's dental arch with associated recorded camera angles for each image. The images may be collected by performing one or more scans of a subject's intraoral cavity using, for example, the intraoral scanning device or camera systems described herein. In some aspects, the intraoral scanner or the camera system can record a plurality of discrete images or a series of continuous images during the scan. Additionally, the position and orientation of the intraoral scanner or the camera system can be tracked and recorded during the scan, and the position and orientation of the intraoral scanner or camera system can further be associated with each respective discrete image or video frame. In another embodiment, a digital model of a patient's dental arch can be access or received (e.g., if the scan was previously performed). The images may include those collected using any of a number of imaging or scanning modalities. For example, the images may be taken using one or more sources of light, such as visible light and/or infrared light (e.g., near IR) sources. The intraoral scanner or camera system is scanned along all surfaces of both the upper and lower jaws to obtain images of all the relevant tooth surface structures. The images received may therefore be part of an image data that may further include the position of the camera from which each image (e.g., camera angle), the modality (e.g., wavelength) used to take each image, and/or other metadata associated with each image. Thus, any of these methods may include accessing (e.g., receiving) the image data including the images.

In general, as used herein a panoramic view refers to a wide-angle view. The panoramic views described herein are not limited to a particular angle (e.g., greater than 30 degrees, greater than 45 degrees, greater than 90 degrees, greater than 135 degrees, greater than 180 degrees, between 10-270 degrees, between 10-225 degrees, between 10-180 degrees, between 30-270 degrees, between 30-225 degrees, etc.).

Referring to operation 1504, the process may include identifying a particular viewing angle for constructing the panoramic view. The particular viewing angle may correspond to the view point in which the panoramic view of the subject's dentition is generated and displayed on the computer screen. The particular viewing angle can be selected by a user. For example, a user may select, via a user interface, whether they would like to inspect the subject's teeth from a buccal, occlusal, lingual, or other perspective (including, as shown in FIGS. 17A-17C and 18A-18B, cylindrical or partially cylindrical projections). In some cases, the user may select multiple viewing angles. The user interface may include a graphical user interface, such as a switch, button, scroll bar, drop-down menu, and/or other graphical user interface elements that allows the user to choose one or more particular viewing angles (perspectives) for viewing the subject's teeth. Alternatively or additionally, the computing device can be configured to automatically select a particular viewing angle, e.g., as a default setting. The apparatuses and methods described herein may allow the user to dynamically change (e.g., in real time) the viewing angle and therefore the panoramic view.

Once the viewing angle is identified, a trace line (e.g., center jaw line) of the images may be identified 1506. The center jaw line may be estimated using the images (e.g., 2D images, such as from the received scanned images), a virtual 3D model of the dentition, and/or position data of the scanner/camera collected during one or more scans of the subject's teeth. A plurality of points (e.g. "virtual pixels") along the center jaw line may be selected or determined, typically (but not necessarily) automatically. In some variations these points (e.g., virtual pixels) may be distributed along the center jaw line, including equally spaced. These virtual pixels may correspond to a point in which the at least one image from the images is collected during the one or more scanning operations can be chosen for generating the panoramic view. Alternatively these points (some or all of them) may be for points between such scanned positions. In some embodiments, the virtual pixels are evenly distributed along the center jaw line. Generally, the denser the distribution of virtual pixels, the more images will be used to generate the panoramic view.

For each of these points (virtual pixels) identified, one or more images from the scanned 2D images may be identified including that point, in which the viewing angle matches or approximately matches the camera angle from which the image was taken 1508. For example, a virtual camera may be passed along a path adjacent to center jaw line. This may be done to identify one or more images having associated camera angles that most closely match the particular viewing angle at each virtual pixel. For example, as the virtual camera passes over a first pixel, one or more images collected during the scanning operation(s) can be identified having a camera angle that is close to the particular viewing angle. As the virtual camera passes adjacent to the center jaw line, at some point, the virtual camera may be perpendicular (or approximately perpendicular) to the virtual pixel (e.g., in the z direction). When the virtual camera is perpendicular to the virtual pixel, the image(s) having camera angle(s) most similar to the particular viewing angle can be selected, thereby selecting the image(s) taken at the most similar position(s) as from the perspective of the particular viewing angle. In some variations the image identified may be a novel, synthesized image, determined for a position corresponding to the viewing angle that has not precise match in the images received.

As (or after) the images are selected, they may be collected 1510. For example, the collected images may be projected onto a virtual screen for each point. The virtual screen can be perpendicular to the viewing direction. This process may be repeated for all of the identified points on the center jaw line (e.g., as the virtual camera passes along the center jaw line over each pixel until a set of identified images) for generating the panoramic view is gathered. For bitewing panoramic views the center jaw line maybe straightened.

At 1512, the set of identified images is used to generate the panoramic view. An approximate panoramic view may be generated using the collected images, which may be arranged along the center jaw line, in the order in which the points along the jaw line are arranged. The panoramic view may be optionally blended to match gradients at boundaries of adjacent images and to provide a more consistent panoramic view to the user 1514. The blending operation may include using target gradients and the positional data associated with the images, as described herein. The final panoramic view may be displayed on a computer display, stored in memory and/or sent as output (e.g., to a network and/or a printer). In some embodiments, the final panoramic view is displayed on a user interface of a display.

Figure 16:
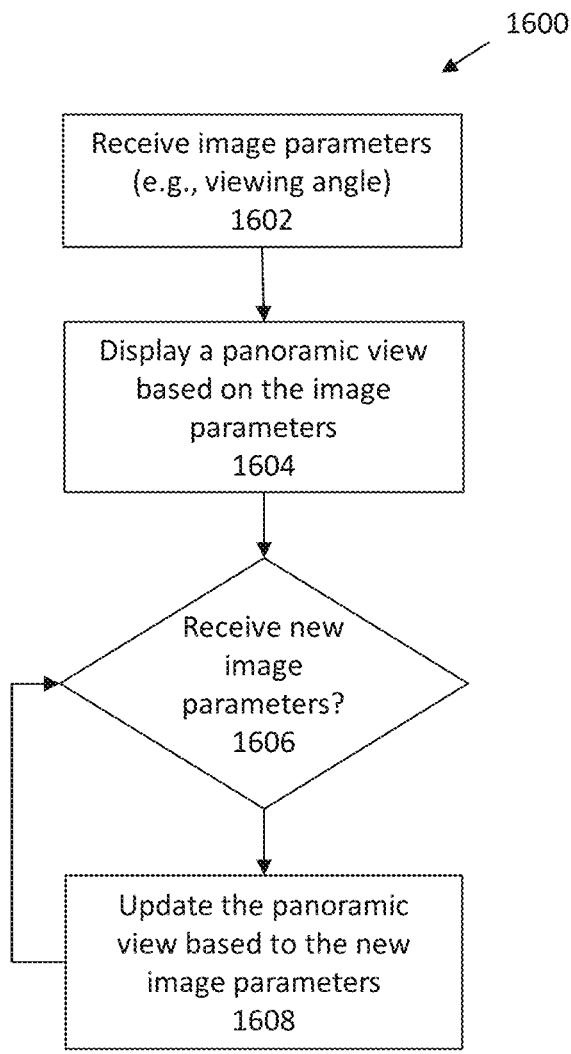
FIG. 16 is a flowchart describing an example of a process for choosing parameters and updating panoramic views of a subject's dentition.

The user interface may include user input features that allow the user to modify the panoramic view based on the viewing angle, the scanning modality, the time of a scan, and/or other image parameters. FIG. 16 illustrates a flowchart 1600 for a process for allowing a user to choose image parameters for displaying a panoramic view of a subject's teeth. Referring to 1602, image parameters are be received, for example, from a user (e.g., via the user interface) and/or set as default parameters. The image parameters may include a particular viewing angle corresponding to a desired perspective for viewing the dentition (e.g., dental arch). The particular viewing angle can, but typically does not, correspond to the camera angle from which the images where taken. The particular viewing angle may be specified as the type of perspective, such as buccal, occlusal or lingual perspectives. Additionally or alternatively, the particular viewing angle may be specified as an angle degree (e.g., 180°, 90°, 70°, 60°, 45°, 30°, 20°, 15°, 10°, 5°, etc.) relative to a given reference, such as the jaw center line. The image parameters may additionally or alternatively include the scanning mode, including the light source range of wavelengths used during the scan(s). In some embodiments, the visible light and/or IR (e.g., near IR) light is used. Visible light images may include surface features of the dentition and IR (e.g., near IR) images may provide internal structural features of the dentition. In some embodiments, the panoramic images are generated using only one scan modality (e.g., visible light or IR) to save computational time in generating the panoramic images. The image parameters may additionally or alternatively include the time in which a scan was taken. For example, a first scan may be taken of the subject's dentition prior to treatment, a second scan may be taken at some time during implementation of a treatment plan, and a third scan may be taken after the treatment plan is complete. A user may desire to view panoramic images from each of the first, second and third scans to analyze the progression of the treatment and/or to decide whether additional treatment is warranted. The user may choose to view the treatment progression sequentially on a display screen using time-lapse or animation, as described herein. The image parameters may additionally or alternatively include a subject's identification so that panoramic images of different dentitions may be viewed and compared.

At 1604, one or more panoramic views is generated based on the image parameters (e.g., user-selected or default) and displayed on the user interface. In one implementation, one or more panoramic views display a dental arch such that the teeth are arranged in a row (e.g., FIG. 12, 13A-13C or 14A-14C). The system can be configured to receive new image parameters 1606 for modifying the panoramic image(s). In some embodiments, the user interface allows the user to change one or more image parameters (e.g., viewing angle, the scanning modality, scan date/time, dentition/subject identification, bitewing/realistic, etc.). This allows the user flexibility in how the panoramic images are displayed and for choosing the best panoramic images for analyzing specific aspects of the dentition. Alternatively or additionally, the system may automatically generate modified panoramic images based, for example, on settings for providing a predetermined arrangement and/or time lapse animations of panoramic images. Once the new image parameters are received, the system can update the panoramic view (or generate one or more new panoramic views) based on the new image parameters 1608. The system can be configured to receive new image parameters for updating the panoramic view and/or displaying new panoramic view(s).

Any of the images and/or virtual models described herein may be rendered using animation and/or time-lapse techniques. For example, the images collected during one or more scans of the teeth may be replayed to the user. The replay may be done in actual time (same time as the scan was performed), increased speed (e.g., 1.25, 1.5, 1.75, 2, 2.25, 2.5 times the scan speed), or decreased speed (e.g., 0.75, 0.5, 0.25, etc. times the scan speed). In some cases, a longitudinal animation can be displayed, where images of the dentition (or a portion of the dentition) of different scans taken at different times are correlated and sequentially displayed to the user. This can show the user what changes have occurred to the dentition over a certain period of time, such as before, during and after an orthodontic treatment.

Any of the images and/or virtual models described here may allow a user to visualize a particular region of interest. A region of interest may include those regions having defects such as caries. In some cases, the system (e.g., processor(s)/controller(s)) can be configured to detect suspected regions of interest in the scanned data. These suspect regions of interest can be indicated in the panoramic views and/or elsewhere on the user interface. The user may label, highlight or otherwise mark those regions that are determined to be regions of interest. In some implementations this detection may be automatically done (e.g., as a default setting). In some cases, the user interface may allow the user to select whether to perform a detection operation and/or select the detection parameters. Such region of interest detection can allow for false positives, with minimal false negatives.

Cylindrical Views

In general, described herein are cylindrical views in which a panoramic view a dental arch may be provided that simultaneously shows two or more of the buccal, lingual and occlusal sides of the teeth, laid out in a flattened panoramic view. This cylindrical view (e.g., a cylindrical view simultaneously showing the lingual, occlusal and buccal sides of the dental arch) may be used for rapid and accurate analysis or comparison of a patient's dental arch. It may also allow a convenient 2D representation (panoramic view) of the entire dental arch. These cylindrical projections may therefore be useful for analysis, storage, and display of the dental arch.

Figure 17A:
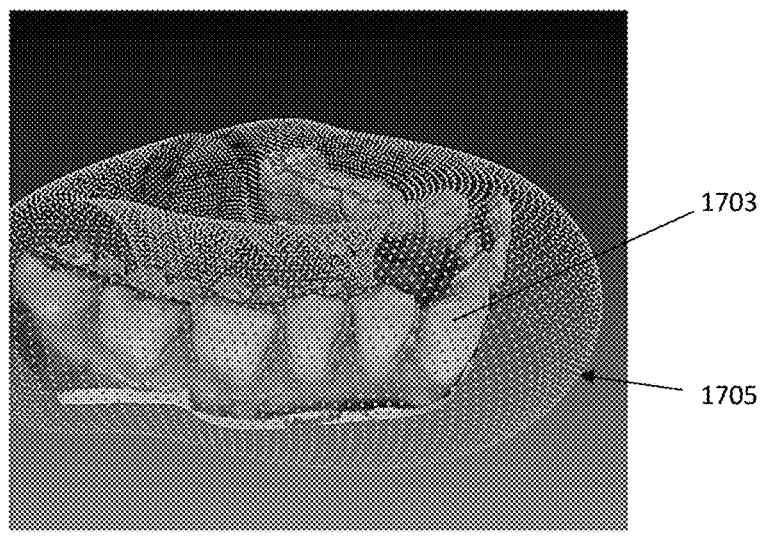
FIGS. 17A-17C illustrate one example of a cylindrical projection of a dental arch that may be generated and/or used in any of the methods and apparatuses described herein.
Figure 17B:
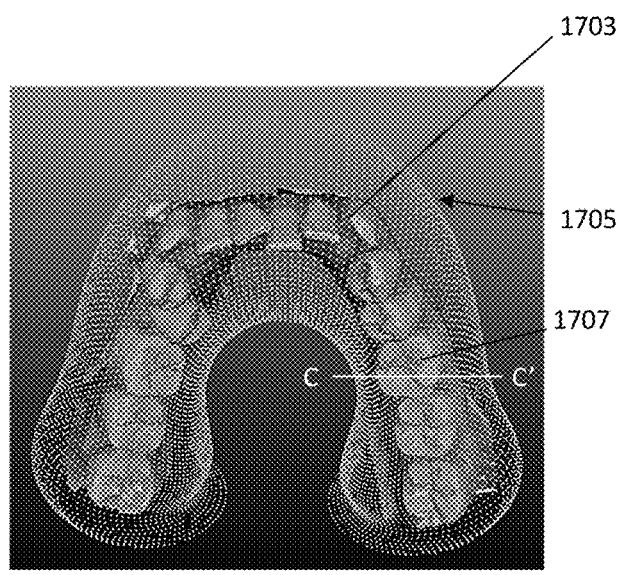
Figure 17C:
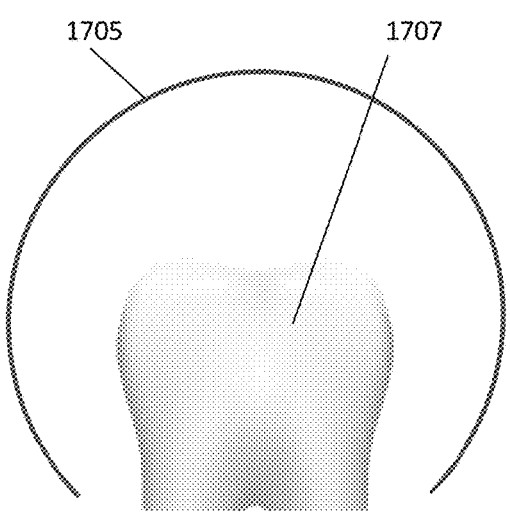

FIG. 17A illustrates one example of a 2D projection of the 3D surface of a patient's dental arch, showing a tube-like (enclosed on three sides) 'screen' 1705 over the dental arch 1703. The virtual screen envelops the dental arch in this example. FIG. 17B shows a top (occlusal) view of the same dental arch and enclosing tube, also showing a section C-C'. FIG. 17C shows the section through line C-C'. This cross-section of the tooth 1707 and screen 1705 in FIG. 17C shows that the tube-like screen encloses the dental arch on three sides (e.g., buccal, occlusal, and lingual), approximately 270 degrees. Other, less enclosing 'screens' may be used, such as 180 degrees, etc. Views taken at each of the points in the enclosing cylinder towards the center line of the teeth may be identified and/or synthesized and stitched together as described herein (including blending) to form a cylindrical mapping of the patient's teeth. The density of the indicated points may be adjusted (increased/decreased) by the user or automatically. For example, the density may be adjusted to prevent loss of detail, while minimized to increase speed.

Figure 18A:
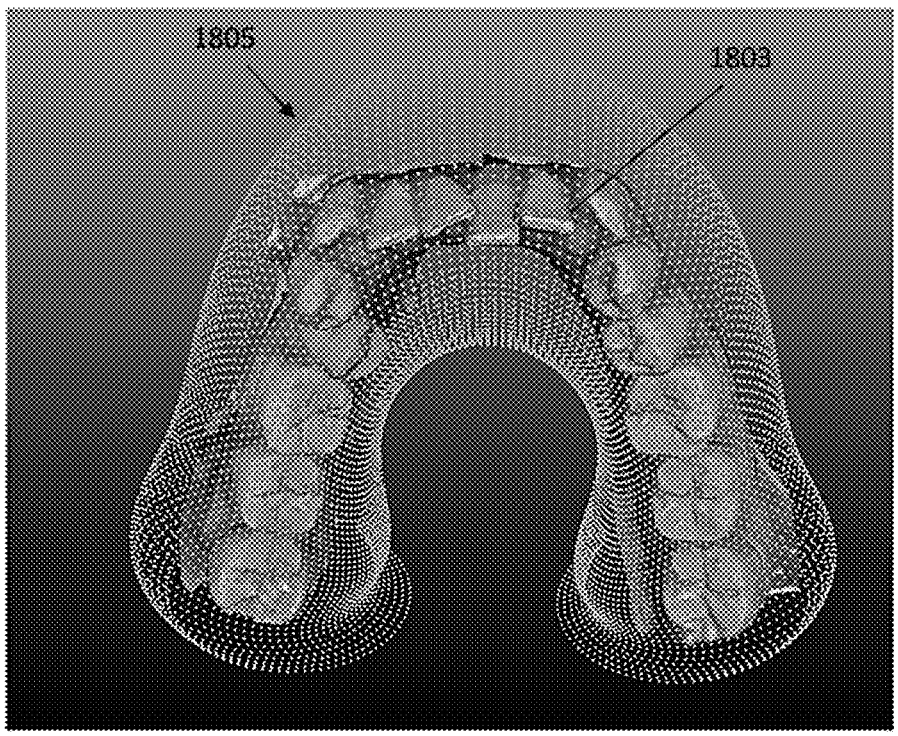
FIGS. 18A and 18B illustrate another example of a cylindrical projection of a dental arch.
Figure 18B:
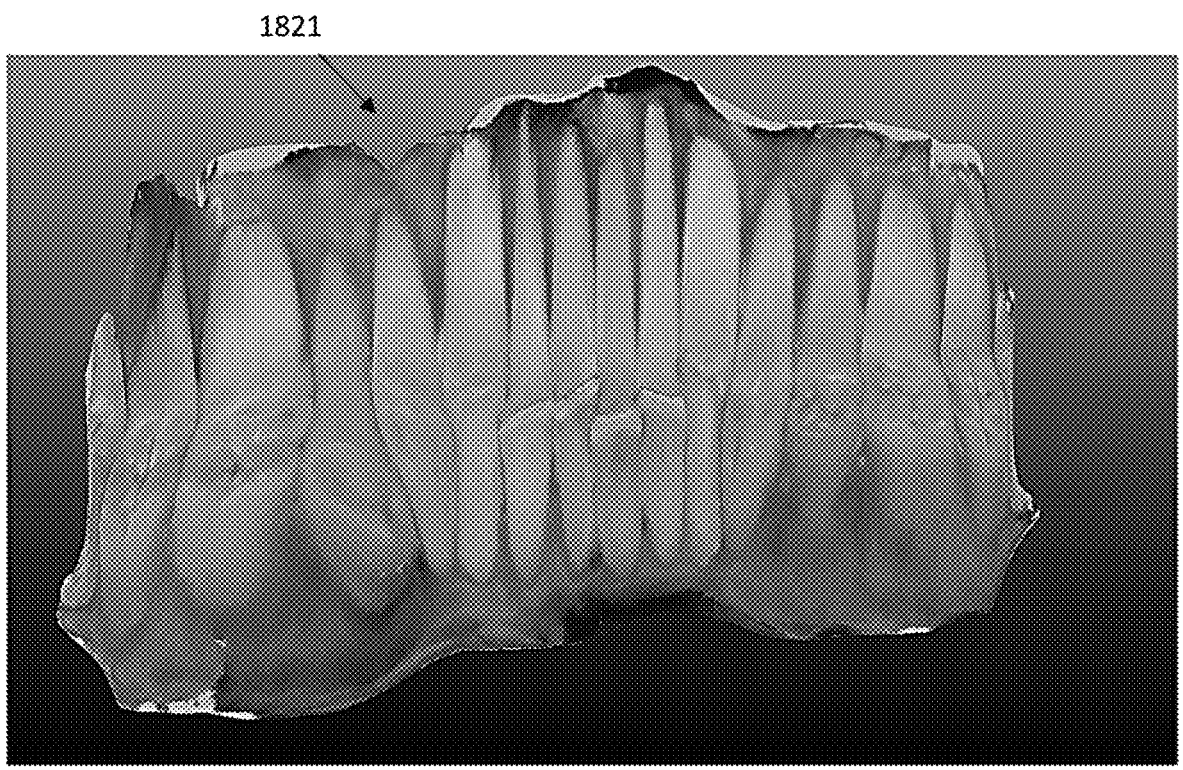

FIGS. 18A-18B illustrate another example of a dental arch shown as a 2D projection of a 3D model of a dental arch 1803 in an occlusal view (FIG. 18A) and, for comparison, a cylindrical projection 1821 (FIG. 18B) showing a cylindrical panoramic view (similar to that described above) of the same dental arch shown in FIG. 18A. In this example, the cylindrical projection 1821 shows lingual, occlusal and buccal faces of the teeth in the same image. Apart from small occlusions, this projection presents all of the visual data in the scan in one image.

The panoramic view shown in FIG. 18B may be generated from a dataset of 2D images taken, e.g., with an intraoral scanner, from recorded or known camera positions, as mentioned above. In some variations, the panoramic view may be identified by using trace lines (e.g., center jaw line) beyond just a single center jaw line; multiple lines may be used.

The cylindrical projections described herein may be useful in part for manual analysis, e.g., by a physician, dentist, etc. In some variations, these projections may be used for machine learning, for example, for machine learning techniques that use images of the dental arch and/or teeth. In such cases, the machine learning engine may use cylindrical projection images of the dental arch for processing by machine learning, (e.g., for one or more of: segmentation, recognition etc.). Including all of the visual data in a single image (e.g., a cylindrical projection) can allow for better machine learning results.

For example, described herein are methods of generating a cylindrical projection of a dental arch that includes processing scanned data (as described above) to form a cylindrical projection of a dental arch including buccal, occlusal, and lingual views. These methods may include determining a trace line or lines that covers all three sides in an overlapping manner, and identifying points on the tubular "screen" around the dental arch, as shown in FIGS. 17A-17B and 18A-18B, and identifying one or more 2D images from, e.g., intraoral scan data (including but not limited to near-IR/IR intraoral scan data, and/or surface scan data), then aggregating these images, e.g., by stitching them together, and blending, smoothing, or otherwise harmonizing them to provide a final panoramic view.

Generating Novel Views from Scan Data

In general, novel view synthesis is the problem of generating novel camera perspectives of a scene given a fixed set of images of the same scene (or overlapping parts of the same scene). Novel view synthesis methods thus deal with image and video synthesis conditioned on camera position. In classical computer vision, image-based rendering (IBR) methods typically rely on optimization-based multi-view stereo methods to reconstruct scene geometry and warp observations into the coordinate frame of the novel view. However, this may result in view-dependent effects, and may result in ghosting-like artifacts and holes. The techniques described herein, which may be referred to as a neural image-based rendering technique, has been particularly adapted for use as described herein. For example, these techniques are adapted for use with intraoral scanning (and comparable medical/dental scanning) inputs, and may be particularly well suited for generating novel views of biological structures, in particular dental structures (e.g., teeth), which may have opacity in both visible light and other penetrating (e.g., near-IR) wavelengths. These techniques may be used with machine learning, which may be trained on reconstructing a learned representation of the scene from the observations, learning end-to-end with a differentiable renderer. This enables learning of priors on geometry, appearance and other scene properties in a learned feature space. Although the techniques described herein may be neural rendering techniques, classical approaches may alternatively or additionally be used.

Neural image-based rendering is a hybrid between classical image-based rendering and deep neural networks that can replace manual heuristics with learned components. A classical IBR method uses a set of captured images and a proxy geometry to create new images, e.g., from a different viewpoint. The proxy geometry is used to re-project image content from the captured images to the new target image domain. In the target image domain, the projections from the source images are blended to composite the final image. This simplified process gives accurate results only for diffuse objects with precise geometry reconstructed with a sufficient number of captured views. However, artifacts such as ghosting, blur, holes, or seams can arise due to view-dependent effects, imperfect proxy geometry or too few source images. To address these issues, neural image-based rendering methods replace the heuristics often found in classical IBR methods with learned blending functions or corrections that take into account view-dependent effects.

As mentioned and described above, the methods and apparatuses herein may generate novel views from the received scan data (e.g., the received plurality of 2D images and corresponding camera position information). Any of these methods and apparatuses may include image-based rendering (IBR) for synthesizing novel views (e.g., of teeth) from sampled views, using contributing images (e.g., preferably 3 images) of the received images, where the contributing images are taken at minimum angle relative to the novel view point. For example, the three (or in some variations, more, e.g., five) contributing images may be selected by a triangulation enclosing the desired (novel) angle or point for which the new, novel, image is to be generated, where the triangulation results in the smallest enclosure that can be formed by the camera positions of the contributing images.

This method may allow for the generating of novel images from a set of images (e.g., the received plurality of scanned 2D images, as may be provided by an intraoral scanner) taken at arbitrary positions. In some variations the use of three such images, which are selected as having camera positions providing the smallest triangle that can enclose the desired novel camera position, has proven to be exceptionally computationally fast, particularly as compared to the use of more (e.g., 4 or more) received images.

The contributing images may then each be broken into multi-plane layers (e.g., RGBα layers). The layers may be sampled evenly in disparity within the contributing image camera view's frustrum. For example, these layers may be formed by re-projecting each plane/layer the sensor plane of a novel view camera and alpha compositing the planes from back to front, encoding a local light field. The adjacent layers of the three (or in some variations more, e.g., 5) contributing images may then be blended. Thus, in some variations the three (or in some variations, more) contributing images may be projected into multiple layers (which may also be referred to as planes) that are parallel to the new viewpoint that they want to produce (e.g., the surface or screen that will be project onto). Then this can be blended, as described above.

The methods described herein may be automated using a machine learning agent (e.g., a novel view generating machine learning agent) that may perform all or some of these steps, including, for example, identifying the contributing images, dividing each contributing image into multi-plane layers, and blending the adjacent layers of the multi-plane layers of the contributing images. In particular, the blending may be performed by a machine learning agent. The machine learning agent may be trained on a dataset, for example, a dental dataset. In some variations the machine learning agent may be trained on a dataset (e.g., a scanned dental dataset) in which a known point, having a known camera position, is removed from the dataset and is used as the target point. The actual image at that known (now target) point may be used. Given the large number of images at known camera positions from a dental scan, many such target training points (images) may be generated, allowing multiple iterations (e.g., thousands, tens of thousands, hundreds of thousands, etc.).

The methods and apparatuses described herein for creating and displaying panoramic views may benefit in particular from the techniques for generating novel views from the received scan data. Novel view generation may relate to the production of new views from a given set of images (where the camera location of each image is also known). The new view or views may be created for a novel camera location for which an image was not captured. For example, novel view generation be used to create new views from multiple (e.g., 3, 4, 5, 6, etc.) images for display and/or for use in generating a panoramic view. The plurality of images, such as images taken with an intraoral scanner, which may also record the camera location to a high degree of accuracy, e.g., using built-in accelerometer or other position sensor(s). These images (which may form an image "soup" including a plurality of images) may be acquired during the scan and additional novel views may be generated from this image soup after post processing.

The generation of novel images of the teeth may be particularly desirable when the plurality of images, e.g., in the scan data, are taken while the teeth are very close to the imaging camera (e.g., the intraoral scanner). For example, a pinhole of a camera (of an scanner) may be, e.g., located ~7 mm above the teeth in some variations, as compared to other scanners (where the teeth may be scanned ~90 mm from the teeth), even where scanner has a very wide angle (which may result in perspective distortions). For example, a typical intraoral scanner may have a of view that spans just a single tooth (where the camera is scanned, e.g., between 1-20 mm from the teeth) or two teeth (where the camera is scanned, e.g., between 25-100 mm from the teeth). Thus, even if the field of view is large enough to cover more than one tooth (e.g., 2-3 teeth) the field of view may be sufficiently narrow so as to limit the perspective of the tooth or teeth within the patient's dentition (e.g., the upper and/or lower dental arch), which may make it difficult to understand from the received images alone the relative position and orientation of the tooth in the jaw and to understand clinical findings in the image. However, despite the relatively small field of view, the scan images acquired may have a very high signal to noise, sharpness, resolution, and other optical properties. In addition, many of these scanned image data sets may include many hundreds and thousands of images.

As a result, the methods and apparatuses described herein, which may permit the formation of relatively large field of view panoramic images from collection of acquired images (e.g., the image soup) for post processing, or from currently (in real-time) scanned multiple images, where the scanner includes multiple, offset imaging cameras (e.g., in some variations 6 or more images may be concurrently imaged), may be used to generate panoramic images and/or novel or synthetic images. For example, in some variations a scanner that is capable of scanning multiple images concurrently, from different offset positions on the scanner (e.g., the wand of the scanner) may be configured, as described herein, to display a novel, synthetic image from a point that is between the multiple cameras on the scanner, including at a central region; this may be particularly helpful where the cameras are offset (e.g., on the sides) of the scanner. Displaying an image from the tip and/or center of the scanning tool (e.g., wand) may be more intuitive than displaying one or more images from cameras on the side of the scanning tool.

FIG. 21 illustrates one example of a method of generating a synthetic image at a novel camera position. As described briefly above, this method may be included as part of a method or apparatus for generating panoramic views. As an initial step, the novel viewpoint may be identified 2101. For example, a novel view direction may be chosen from the received scan data. FIG. 19 is an illustration showing the selection of a novel view direction 1901 (shown in black) as compared to three input images 1903, 1905, 1907 (shown in gray). Three (or in some variations, more, such as five) contributing images may be chosen from the image data set 2103. For example, the three images may be chosen based on the position of the camera, so that the three images are looking at the same scene, and their chief ray directions form a triangle which contains the chief ray direction of the desired synthesized image. This may be alternatively expressed as choosing the contributing images as the set of images from the data set having camera positions forming a triangle (when three images are used) enclosing the novel viewpoint with the smallest enclosing area. Alternatively or additionally, this may be understood as the set of images having the smallest difference in the angle relative to the viewpoint angle of the novel viewpoint. In some variations, both of these conditions may be true (e.g., having both the minimal area enclosing camera position of the novel view and also pointing in approximately the same direction (having a minimal angular difference relative to the novel viewpoint.

In some variations, the method or apparatus for determining the novel view may also require that the contributing images (e.g., forming the surrounding triangle formation) may each have an area field of view in a distance of ~10 mm from the camera (e.g., pinhole camera) intersection will be more that about 0.5 of the union of the field of views area. For example, FIG. 20 illustrates the intersection over union, showing an intersection over union of greater than one-half (0.5). The intersection over union is an evaluation metric that may be used to measure the accuracy of an object detector on a particular dataset.

After determining the contributing images from the image data set, they may be transformed into multi-plane layers 2105, for example, by projecting to a grid which contains a number of planes parallel to the screen of the novel viewing camera. Each point in the screen may correspond to a pixel on the novel view image. In some variations, after the contributing images from the input images are projected on the grid they may result in a tensor of size image width X image height X number of planes X 3. The adjacent layers of the transformed multi-layered contributing images may then be blended 2107 to form the novel viewpoint image.

As mentioned above, in any of these methods and apparatuses, a machine learning agent may be trained and used, e.g., to blend the layers of the contributing images. For example, a machine learning agent may be trained using the plurality of scan images received (e.g., from the intraoral scanner), by a "leave one out" method, in which one image is removed and the camera position for the removed image is used as the true ("ground truth") image when using three neighboring images and trying to predict the image which was removed.

Figure 22A:
FIG. 22A-22E show one example of the generation of a novel, synthesized image from a dataset including intraoral scanned data.
Figure 22B:
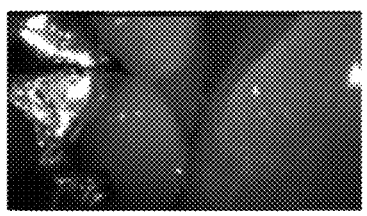
Figure 22C:
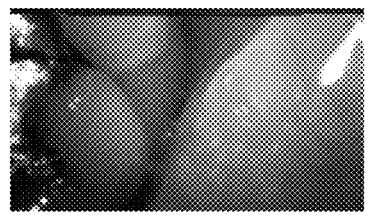
Figure 22D:
Figure 22E:
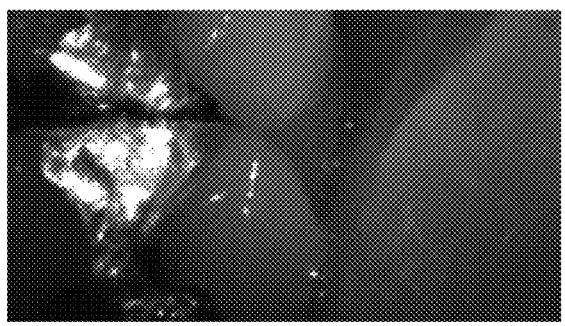
Figure 23A:
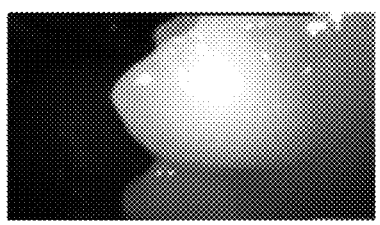
FIGS. 23A-23E show another example of the generation of a novel, synthesized image from a dataset including intraoral scanned data.
Figure 23B:
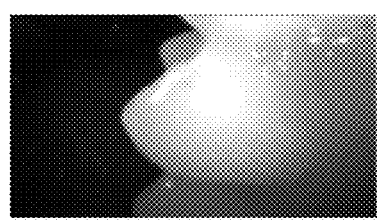
Figure 23C:
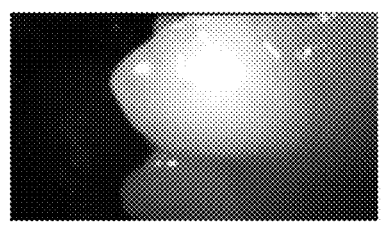
Figure 23D:
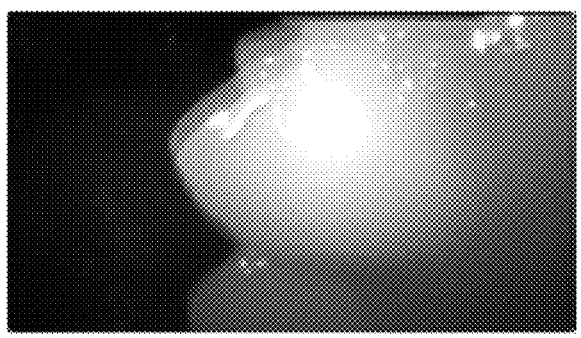
Figure 23E:
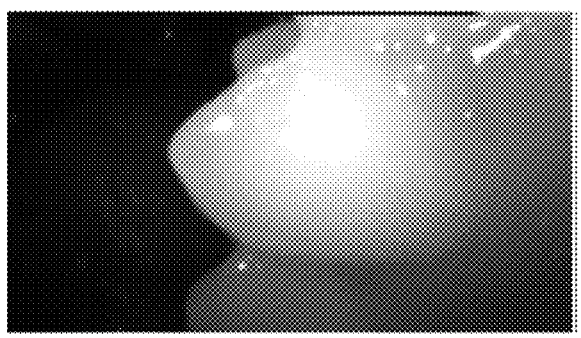

FIGS. 22A-22E and 23A-23E illustrate examples of prototype projections using a trained machine learning agent. For example, FIGS. 22A-22C illustrate examples of three contributing images, identified from a dataset including a plurality of scanned images, each with corresponding camera position information. The three contributing images were each shown to have approximately the same view angle relative to the novel view to be determined (e.g., have a minimal difference relative to the novel viewpoint angle), and form a minimal triangle enclosing the novel viewpoint. Each of these contributing images were then transformed into multiple parallel planes (e.g., RGBα layers) and blended to for an image at the novel viewpoint, as shown in FIG. 22D, showing a predicted image for the novel viewpoint. This predicted image favorably compared to the actual (ground truth) image at that viewpoint, shown in FIG. 22E. Similar results were seen in the example of FIG. 23A-23E. The three contributing images are shown in FIGS. 23A-23C, and the predicted image is shown in FIG. 23D. For comparison the actual (ground truth) image is shown in FIG. 23E.

In these examples, a trained machine learning agent (network) was used for blending, which was simple and fast. This technique may be used in particular for determining images for panoramic views, as mentioned above.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intraoral scanning system for generating a synthetic view from a plurality of intraoral scanning views, the system comprising:
   a wand configured to be moved over a subject's dental arch to generate a plurality of two-dimensional (2D) images of the subject's dental arch, each taken at associated camera angles and positions; and
   one or more processors including a memory storing computer-readable instructions configured to cause the one or more processors to execute a method comprising:
      identifying a synthetic viewpoint having a synthetic camera angle and a synthetic camera position relative to the dental arch;
      identifying one or more contributing images from the plurality of 2D images, wherein the one or more contributing images have a minimal angle relative to the synthetic camera angle of the synthetic viewpoint;
      forming the synthetic view from the one or more contributing images based on the synthetic viewpoint; and
      displaying all or a portion of the synthetic view.

2. The system of claim 1, wherein the method further comprises identifying the synthetic viewpoint by a position in space corresponding to the synthetic camera position and synthetic camera angle.

3. The system of claim 1, wherein identifying one or more contributing images comprises identifying three or more contributing images.

4. The system of claim 1, wherein identifying the synthetic viewpoint comprises receiving a point selected by a user from a user interface.

5. The system of claim 1, wherein identifying one or more contributing images comprises confirming that an intersection over union for each of the one or more contributing images is greater than 0.5.

6. The system of claim 1, wherein the contributing images have a minimal angle relative to the synthetic camera angle of the synthetic viewpoint that is 5 degrees or less.

7. The system of claim 1, wherein forming the synthetic view comprises transforming the contributing images into multi-plane layers and blending the multi-plane layers to form the synthetic view.

8. The system of claim 7, wherein blending comprises applying a trained machine learning agent to blend adjacent multi-plane layers of the contributing images to form the synthetic view.

9. The system of claim 8, wherein the trained machine learning agent is trained on a plurality of intraoral scanning views.

10. The system of claim 1, wherein the one or more contributing images comprises a plurality of contributing images and wherein the synthetic camera position of the synthetic viewpoint is bounded by the camera positions of the plurality of contributing images.

11. An intraoral scanning system for generating a synthetic view from a plurality of intraoral scanning views, the system comprising:
   a wand configured to be moved over a subject's dental arch to generate a plurality of two-dimensional (2D) images of the subject's dental arch, each taken at associated camera angles and positions; and
   one or more processors including a memory storing computer-readable instructions configured to cause the one or more processors to execute a method comprising:
      identifying a synthetic viewpoint having a synthetic camera angle and a synthetic camera position relative to the dental arch;
      identifying a plurality of contributing images from the plurality of 2D images, wherein the plurality of contributing images have a minimal angle relative to the synthetic camera angle of the synthetic viewpoint and wherein the synthetic camera position of the synthetic viewpoint is bounded by the camera positions of the plurality of contributing images;

forming the synthetic view from the plurality of contributing images based on the synthetic viewpoint; and displaying all or a portion of the synthetic view.

12. The system of claim 11, wherein the method further comprises identifying the synthetic viewpoint by a position in space corresponding to the synthetic camera position and synthetic camera angle.

13. The system of claim 11, wherein identifying plurality of contributing images comprises identifying three or more contributing images.

14. The system of claim 11, wherein identifying the synthetic viewpoint comprises receiving a point selected by a user from a user interface.

15. The system of claim 11, wherein identifying the plurality of contributing images comprises confirming that an intersection over union for each of the plurality of contributing images is greater than 0.5.

16. The system of claim 11, wherein the contributing images have a minimal angle relative to the synthetic camera angle of the synthetic viewpoint that is 5 degrees or less.

17. The system of claim 11, wherein forming the synthetic view comprises transforming the contributing images into multi-plane layers and blending the multi-plane layers to form the synthetic view.

18. The system of claim 17, wherein blending comprises applying a trained machine learning agent to blend adjacent multi-plane layers of the contributing images to form the synthetic view.

19. The system of claim 18, wherein the trained machine learning agent is trained on a plurality of intraoral scanning views.

20. An intraoral scanning system for generating a synthetic view from a plurality of intraoral scanning views, the system comprising:

a wand configured to be moved over a subject's dental arch to generate a plurality of two-dimensional (2D) images of the subject's dental arch, each taken at associated camera angles and positions; and one or more processors including a memory storing computer-readable instructions configured to cause the one or more processors to execute a method comprising:

identifying a synthetic viewpoint having a synthetic camera angle and a synthetic camera position relative to the dental arch;

identifying a plurality of contributing images from the plurality of 2D images, wherein the plurality of contributing images are selected from the plurality of 2D images as having been taken from a camera angle and camera position that are closest to the synthetic camera angle and synthetic camera position;

forming the synthetic view from the plurality of contributing images based on the synthetic viewpoint; and displaying all or a portion of the synthetic view.

* * * * *